United States Patent
McKenna et al.

(10) Patent No.: US 7,527,733 B2
(45) Date of Patent: May 5, 2009

(54) CHELATING AGENTS FOR HEAVY METAL REMOVAL

(75) Inventors: Charles E. McKenna, Pacific Palisades, CA (US); Boris A Kashemirov, Los Angeles, CA (US); Isabelle Favier, St. Thibault des Vignes (FR); Thomas D. Wolfe, Rough & Ready, CA (US)

(73) Assignee: The University of Southern California, Los Angeles, CA (US)

( * ) Notice: Subject to any disclaimer, the term of this patent is extended or adjusted under 35 U.S.C. 154(b) by 148 days.

(21) Appl. No.: 10/957,553

(22) Filed: Sep. 30, 2004

(65) Prior Publication Data

US 2006/0065604 A1 Mar. 30, 2006

(51) Int. Cl.
*C02F 1/42* (2006.01)

(52) U.S. Cl. ........................ 210/263; 210/912; 502/402; 558/172; 560/168; 562/17

(58) Field of Classification Search ................... 210/263
See application file for complete search history.

(56) References Cited

U.S. PATENT DOCUMENTS

| | | | | |
|---|---|---|---|---|
| 5,182,251 A | | 1/1993 | Bruening et al. | 502/401 |
| 5,948,931 A | | 9/1999 | McKenna et al. | 558/172 |
| 5,980,716 A | * | 11/1999 | Horinouchi et al. | 204/524 |
| 6,432,313 B2 | * | 8/2002 | Bruening et al. | 210/670 |
| 7,083,731 B2 | * | 8/2006 | Ekman et al. | 210/666 |

FOREIGN PATENT DOCUMENTS

WO    WO/01/23067 A1    5/2001

OTHER PUBLICATIONS

Carrick, "Novel Troika Acid Derivatives: Photochemistry and Metal Chelation", dissertation from *University of Southern California*, 2000, pp. 1-158.

Carrick, et al., "Indirect Photo-Induced Phosphorylation Via a C-Ester Caged Troika Acid", *Phosphorus, Sulfur, and Silicon*, vol. 147, 1999, p. 65.

Carrick, et al., "Indirect Photo-Induced Phosphorylation Via a Photoabile Troika Acid C-Ester: *o*-Nitrobenzyl (*E*)-(Hydroxyimino)(dihydroxyphosphinyl)acetate", *Tetrahedron*, vol. 56, 2000, pp. 2391-2396.

Gibson, et al. Metal Complexes of α-Hydroxyimino Phosphonic Acid Derivatives. Separation of the *E* and *Z* Isomers by Metal Chelation and the Preparation and Characterization of Copper Bis[(*E*)-(α-(hydroxyimino)benzel)phosphonate]-Water., *Inorg. Chem.*, 28, 1928-1932, (1989).

(Continued)

*Primary Examiner*—Peter A Hruskoci
(74) *Attorney, Agent, or Firm*—Kilpatrick Stockton LLP

(57) ABSTRACT

The present invention provides for Troika acids attached to a macroporous resin and Methods of preparing the same, including direct attachment of a Troika acid, and attachment of a Troika acid precursor followed by generation of the Troika acid in situ. Methods of functionalizing a resin to facilitate attachment are also described. Multiple Troika acids, comprising a pair of Troika acids joined together are described. Synthetic routes to both microporous and macroporous resins modified by introduction of a suitable Troika-type acid have been designed and validated. In a preferred embodiment, a macroporous Troika resin removes $Cu^{2+}$ and $Ni^{2+}$ from aqueous solution with high affinity, and is selective against $Mg^{2+}$ or $Ca^{2+}$. The materials of the present invention have advantages for metal removal from power plant waste water.

14 Claims, 12 Drawing Sheets

OTHER PUBLICATIONS

Kashemirov, et al., ""Troika Acids": Synthesis, Structure, and Fragmentation Pathways of Novel α-(Hydroxyimino)phosphonoacetic Acids", *J. Am. Chem. Soc.*, vol. 117, 1995, pp. 7285-7286.

Kashemirov, et al., ""Troika Acids": Synthesis, Structure, and Fragmentation Pathways of Novel α-(Hydroxyimino)phosphonoacetic Acids", *J. Am. Chem. Soc.*, vol. 117, supp. 1995, pp. 1-33.

Kashemirov, et al., "Troika Acid Derivatives: Multifunctional Ligands for Metal Complexation in Solution and on Solid Supports, a Novel, Linear Trinickel ("Troitsa") Complex", *Phosphorous, Sulfur and Silicon*, vol. 177, 2002, p. 2273.

Kashemirov, et al., "(E)-(Hydroxyimino)(hydroxymethoxyphosphinyl)acetic Acid: Synthesis and pH-Dependent Fragmentation", *Tetrahedron Letters*, vol. 36 No. 52, 1995, pp. 9437-9440.

Kashemirov, et al., "Effects of Divalent Metal Ions on pH-Dependent Hydrolysis of p-Nitrophenyl (E)-(Hydroxyimino)Phosphonoacetate", *Phosphorus, Sulfur, and Silicon*, vol. 147, 1999, p. 153.

Khokhlov, P. S.; Kashemirov, B. A.; Strepikheev, Y. A., "Nitrosation of Phosphono- and Phosphinoacetic Acid Esters", *J. Gen. Chem. USSR* (Engl.), 52, 2468-2469.

Luftor, et al., "Extraction of Heavy Metals from Waste Water By Polymeric Chelating Resins", *University of Colorado*, Feb. 4, 2004.

McKenna, et al., "(Hydroxyimino)phosphonoacetic Acids: Synthesis, Stereochemistry and Reactivity", *Phosphorus, Sulfur, and Silicon*, vol. 111, 1996, p. 158.

McKenna, et al., "(E/Z) Stereoisomer Assignment by $^{13}$C NMR in Trifunctional Phosphonate α-Oximes and α-Arylhydrazones", *J. Chem. Soc., Chem. Commun.*, 1994, pp. 1211-1212.

McKenna, et al., "Facile Dealkylation of Diakylphosphonates by Bromotrimethylsilane", *Tetrahedron Letters*, 155-158, (1977).

McKenna, et al., "Functional Selectivity in Phosphonate Ester Dealkylation with Bromotrimethylsilane", *J. Chem. Soc., Chem. Comm.*, 739, (1979)).

Wakley, J, "Removal of Heavy Metals From Waste Water", *Brigham Young University*, Feb. 4, 2004.

International Search Report mailed Jul. 13, 2006 corresponding to PCT/US05/34420.

Written Opinion of the International Searching Authority mailed Jul. 13, 2006 corresponding to PCT/US05/34420.

Bodsworth, C., "The Extraction and Refining of Metals," Department of Materials Technology, Brunel University, 1994, pp. 259-260.

Breuer, E., "Acylphophonates and their derivatives," Chemistry of Organophosphorous Compounds, John Wiley & Sons, 1996, p. 685.

Elkot, A. M., "Solvent Extraction of Neodymium, Europium and Thulium by Di-(2-ethylhexyl)Phosphoric Acid," J. Radioanalytical and Nuclear Chemistry, 1993, vol. 170, pp. 207-214.

Farmer, M. F. et al., "Complexation Properties of Phosphonocarboxylic Acids in Aqueous Solutions," Journal of Solution Chemistry, 1981, vol. 10, pp. 523-532.

Felix, A., et al., "Rapid Fluorometric Detection for Completeness in Solid Phase Coupling Reactions," Analytical Biochemistry, 1973, vol. 52, pp. 377-381.

Johnson, C.R. et al., "Solid Phase Synthesis of Alkenes Using the Horner-Wadsworth-Emmons Reaction and Monitoring by Gel Phase 31P NMR," Tetrahedron Letters, 1995, vol. 36, pp. 9253-9256.

Kakoi, T. et al., "Separation of Cobalt and Nickel by Liquid Surfactant Membranes Containing a Synthesized Cationic Surfactant," Separation Science and Technology, 1998, vol. 33, pp. 1163-1180.

Mather, J. N. et al., "Recovery of Neptunium from Highly Radioactive Waste Solutions of Purex Origin Using Tributyl Phosphate," Separation and Science Technology, 1996, vol. 31, pp. 2045-2063.

McKenna, C. E. et al., "Innovative Chelating Agents for Heavy Metal Removal," Product ID # MP-2/W06530, May 2003.

Motekaitis, R. J. et al., "Best—A new program for rigorous calculation of equilibrium parameters of complex multicomponent systems," Can. J. Chem, 1982, vol. 60, pp. 2403-2409.

Lockwood Greene Engineers, "Power Plant Wastewater Treatment Technology Review Report," WSSI 1996, pp. A1-1 through A1-3.

Sliva, T. Y. et al., "Copper(II) and nickel(II) complexes with some oxime analogs of amino acids. Potentiometric, spectroscopic and X-ray studies of complexes with 2-cyano-2-(hydroxyimino)acetic acid and its ethane-1,2-diamine derivative," J. Chem. Soc., 1998, pp. 1863-1867.

Sliva, T. Y. et al., "Co-ordination ability of amino acid Oximes. Potentiometric, spectroscopic and structural studies of complexes of 2-cyano-2-(hydroxyimino)acetamide," J. Chem. Soc., 1997, pp. 273-276.

Song, B. et al., "Metal-Ion-Coordinating Properties of a Viral Inhibitor, a Pyrophosphate Analogue, and a Herbicide Metabolite, a Glycinate Analogue: The Solution Properties of the Potentially Five-Membered Chelates Derived from Phosphonoformic Acid and (Aminomethyl)phosphonic Acid," Helvetica Chimica ACTA, 1994, vol. 77, pp. 1738-1756.

Stunzi, H. et al., "Stability Constants of Metal Complexes of Phosphonoacetic Acid," Journal of Inorganic Biochemistry, 1979, vol. 10, 309-316.

\* cited by examiner

R= $H_2N(CH_2)_n$, n = 2 - 10;
Z = O, N(H), S.

I

II

CHELATING AGENTS FOR HEAVY METAL REMOVAL

FIELD OF THE INVENTION

The present invention generally relates to chelating agents for removal of heavy metals from aqueous media. In particular, the present invention relates to chelating agents that can be linked to a resin.

BACKGROUND

Potable water is a precious resource, yet it is one that is increasingly under threat from a torrent of polluters. Amongst the countless man-made contaminants that infiltrate our water sources are heavy metals. Usually as byproducts of industrial processes, if ingested in even trace amounts, these materials pose many serious health risks to humans, risks that include damage to internal organs, the central nervous system and the reproductive system, as well as side effects such as nausea and vomiting.

In the last three decades, in response to a growing awareness of the hazards presented by pollutants in the water supply, governments have enacted legislation to control discharges of waste. In particular, major acts, such as the Clean Water Act, identified heavy metals as substances requiring aggressive regulation. Consequently, industries, ranging from metal mining, manufacturers of computers and other electronic components, producers of fertilizers, to power generation facilities, have sought various means to remove metal ions from their waste streams before they reach natural bodies of water.

Amongst the methods of heavy metal extraction currently practiced are precipitation (often using electrochemical cells), reverse osmosis, use of paramagnetic nanoparticles, biological degradation by specially engineered bacteria, and ion exchange. The last of these, ion exchange, is particularly attractive to producers of large volumes of waste, especially those in the power generation industry which produces vast quantities of water contaminated with heavy metals every day.

Ion exchange is a separation process that has found profitable application in separation of closely similar metal ions. The underlying principles of ion exchange technology, and examples of typical resins, are familiar to one of ordinary skill in the art (see, e.g., *Principles and Practice of Analytical Chemistry*, F. W. Fifield, and D. Kealey, International Textbook Company, (1983), at pages 130-138). In brief, ion exchange apparatuses comprise an insoluble stationary phase—usually a porous resin—attached to which are fixed charge-carrying groups. Mobile counter ions of opposite charge reversibly exchange with solute ions in a mobile phase that travels across the resin. Variations in reversible exchange rate give rise to differential mobilities.

Accordingly, ion exchange has been applied to waste streams from a number of industrial processes. For example, ion exchange is widely used for polishing operations to reduce residual heavy metal and other pollutants to very low levels in order to meet National Pollutant Discharge Elimination System (NPDES) permit requirements or to satisfy the stringent quality thresholds required for re-use of waste products. Solid phase methods based on ion-exchange resins have provided very convenient application and recovery of the extractant and are particularly appropriate for removal of heavy metal contaminants from non-nuclear power plant effluents, where ready regeneration of the saturated resin is desirable and where introduction of toxic organic solvents into the environment must be avoided. Examples of chelating agents that have been deployed for heavy metal sequestration include dithiocarbamates.

There are two principal advantages of ion exchange processes. One is that quality effluent is attainable; a second is that specific species can be targeted for removal. However, a major disadvantage of current ion exchange technology, apart from that inherent in any batch process, is the relatively large volume of acidic wastes and flush waters that are needed. The attendant hazards of handling concentrated acids (and bases) have also been recognized.

Despite those disadvantages of current systems, ion exchange remains a technology of interest. Important characteristics of an ideal wastewater treatment resin would include: 1) high affinity for the target metal ions, which may be present in wastewater at relatively low concentrations (e.g., <100 ppm); 2) relatively low affinity for other metal cations, to avoid premature inactivation of the resin that would lead to increased regeneration cycles; and 3) variable metal affinity in response to some easily changed system parameter, such as the pH. Commonly, simple cation exchange resins exhibit deficiencies in one or more of these areas. For example, benzenesulfonate resins have relatively low heavy metal affinities and selectivities and require strong acids to release other bound metal ions when they are regenerated. Needless to say, the concentrated mineral acid required for the regeneration process poses operator safety, corrosion and disposal issues.

In some types of ion exchange processes, complexing agents with chelating functional groups that have selective affinities for certain metal ions are attached to the resin. With suitable choice of chelating group, target metal ions can be slowed sufficiently in their passage across the resin that they are effectively sequestered. Thus, the use of organic complexing agents for the selective removal and recovery of metal ions from aqueous solutions is a proven technique, and both solid support and immiscible liquid extraction have been utilized (see, e.g., Rydberg, J.; Musikas, C.; Chippin, R. G., *Principles and Practices of Solvent Extraction*, New York, (1992)).

Before considering whether a complexing agent is suitable for use with a resin, it is typical to consider its properties in solution. The usual categories of compounds currently used as extractants for heavy metal ions in various liquid-liquid extraction methods are: 1) α-hydroxyoximes; 2) phosphorus-bonded oxygen-donor compounds; and 3) acidic organophosphorous compounds (see, e.g., Kakoi, T.; Ura, T.; Kasaini, H.; Goto, M.; Nakashio, F., "Separation of Cobalt and Nickel by Liquid Surfactant Membranes Containing a Synthesized Cationic Surfactant", *Separation Science and Technology*, 33, 1163-1180, (1998); Elkot, A. M., "Solvent Extraction of Neodymium, Europium and Thulium by Di-(2-ethylhexyl) phosphoric acid", *J. Radioanalytical and Nuclear Chemistry-Articles*, 170, 207-214, (1993); Mathur, J. N.; Murali, M. S.; Krishna, M. V. B.; Iyer, R. H.; Chinis, R. R., et al., "Solutions of Purex Origin using Tributyl-phosphate", *Separation Science and Technology*, 31, 2045-2063, (1996)).

The oxime, or hydroxy-imino, function strongly binds metal ions, particularly transition metal ions. This function has been used primarily in liquid-liquid extractions of metals, with extractant molecules that incorporate both a hydroxy group and the oxime to enable bidentate chelation.

Neutral organophosphorous esters have demonstrated the ligating power of the neutral phosphonate group, which is due to its high polarity. For example, the tri-n-butyl phosphate group is highly polar, having a dipole moment of 3.0 Debye units and a relatively high dielectric constant (8.0), and has been extensively used as an extractant for actinides and lanthanides (see, e.g., De, A. K.; Khopkar, S. M.; and Chalmers, R. A., *Solvent Extraction of Metals*, p. 259, Van Nostrand Reinhold Company, New York, (1970)). Neutral organophosphorous esters solvate electrically neutral metal-anion ion pairs, formed by suppression of their ionization in aqueous solution, and, therefore, function satisfactorily only in the presence of a highly concentrated salting-out electrolyte. The high extractive power of these reagents has been demonstrated for a large number of metal salts, typically nitrates and chlorides (see, e.g., Marcus, Y.; Kertes, A. S., *Ion Exchange and Solvent Extraction of Metal Complexes*; (p. 1037 of the 1970 edition); Wiley Interscience, New York, 1969). However, neutral organophosphorous esters have had no direct relevance to heavy metal abatement in industrial effluents hitherto principally because the phosphonate group has very little chelating power.

Simple acidic organophosphorous reagents extract metals in aqueous solution essentially by a cation exchange reaction between the replaceable proton of a phosphonic acid OH group and the coordinating metal cation. In the majority of extraction processes that utilize these reagents, the phosphonic acid $RP(O)(OH)_2$ group entering into the exchange reaction is only singly-ionized, i.e., one of the protons remains unexchanged. In organic solvents, dialkyl phosphoric monoacids are usually dimers, and the resulting metal chelates are generally represented as $M(HA_2)$. Typically, these reagents have been used in liquid-liquid extractions and thus incorporate long lipophilic 'tails': e.g., monododecyl-phosphonic acid, used for extraction of U(VI) or Fe(III), and mono-n-butyl-, monoisobutyl- and monoisoamyl-phosphonic acids, used for extraction of protactinium (see Bodsworth, C., *The Extraction and Refining of Metals*, CRC Press, London, (1994)).

Given the success of these organic ligands with single functional groups as chelating agents for heavy metal ions, attempts have been made to incorporate two or more groups into a single ligand. As is well understood, bidentate ligands offer significant thermodynamic advantages over mono-dentate ligands, a property referred to as the "chelate effect" (see, e.g., F. A. Cotton, and G. Wilkinson, *Advanced Inorganic Chemistry*, (4th ed., Wiley, 1980), at page 71). Principally, there is an entropic benefit from taking half as many bidentate ligands out of solution into a complex as monodentate ligands would be taken. Additionally, of course, fewer molar equivalents of a bidentate ligand are required to achieve the same chelating effect as for a monodentate ligand.

β-hydroxyoximes are highly selective metal complexing reagents that preferentially chelate ions of nickel, molybdenum, copper and certain other transition metal ions. The oxime group increases the acidity of the neighboring alcohol group, thereby enhancing bidentate ligation. The extraction equilibrium can be represented by equation (1):

$$M^{2+}(aq)+2RH(org)=R_2M(org)+2H^+(aq) \quad (1)$$

Equation (1) shows that the OH protons on the ligand (denoted RH) exchange with the metal ions, the equilibrium position being governed by the overall hydrogen ion concentration. Structure 1 is a typical β-hydroxyoxime reagent that has been used to extract metal ions from acid solutions. Exemplary alkyl substituents, denoted R, include $C_9H_{19}$ and $C_{12}H_{25}$.

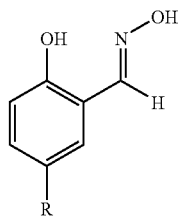

1

Oxime and phosphonate groups can be combined into a single molecule to form a free bidentate ligand for metals (see, e.g., Breuer, E., *Acylphosphonates and Their Derivatives: The Chemistry of Organophosphorous Compounds*, p. 685, John Wiley & Sons, New York, (1996)). In general, the simple α-(hydroxyimino)phosphonic acids and their monoesters have been made as E isomers only, see Breuer, E., *Acylphosphonates and Their Derivatives: The Chemistry of Organophosphorous Compounds*, p. 685, John Wiley & Sons, New York, (1996). Examples in which the ligand coordinates to the metal in a bidentate chelating mode through the oxime nitrogen atom and a phosphonate (P=O) oxygen atom, include: the diester, diethyl (E)-α-hydroxyimino-p-methoxy-benzylphosphonate, which forms isolable complexes with Co, Ni and Cu dications; and the E isomer of monoester monoacid phosphonate versions of these complexes that contains one available POH group and one POR ester group (where R is an alkyl group, for example, ethyl). Formation constants and metal binding selectivities have not been reported for these ligands.

Phosphonocarboxylates have been reported to have enhanced complexation properties. Phosphonoacetic acid (PAA), which has found limited use as an extraction agent for some lanthanide series elements, was found to ligate a range of metal dications (see, e.g., Farmer, M. F.; Heubel, P.-H. C.; Popov, A. I., "Complexation Properties of Phosphonocarboxylic Acids in Aqueous Solutions", *J. Solution Chemistry*, 10, 523-532, (1981); and Stunzi, H.; Perrin, D. D. J., *Inorg. Biochem.*, 10, 309-318, (1979)). Complexation with such ligands involves intramolecular coordination by both the phosphonate and the carboxylate groups. $Cu^{2+}$ is especially tightly bound by such ligands, with a $K_f$ (equilibrium complex formation constant) of $10^8$, but alkaline earth dications are less well bound, having $K_f$ values of around $10^2$-$10^3$. Thus, these species have high discriminating power for various cations. Transition metals are preferentially bound by the trianionic form of the ligand prevalent at pH >~6-7. The related phosphonocarboxylate, phosphonoformic acid, complexes transition metals about as well as pyrophosphate at slightly alkaline pH, despite the higher negative charge of pyrophosphate under such conditions, thus confirming the superior complexing power of the phosphonocarboxylate ligand (see, Song, B.; Chen, D.; Bastian, M.; Martin, B. R.; Sigel, H., "Metal-Ion-Coordinating Properties of a Viral Inhibitor, a Pyrophosphate Analogue, and a Herbicide Metabolite, a Glycinate Analogue", *Helvet. Chim. Acta*, 77, 1738-1756, (1994)).

The combination of neighboring oxy-imino and carboxyl groups in a single ligand can also lead to markedly enhanced chelating ability. Thus, 2-cyano-2-(hydroxyimino) acetic acid, 2-cyano-2-(hydroxyimino)acetamide and 2-(hydroxyimino) propanohydroxamic acid have been found to be powerful ligands for both $Cu^{2+}$ and $Ni^{2+}$ (see, e.g., Sliva, T. Y.; Duda, A. M.; Glowiak, T.; Fritsky, I. O.; Amirhanov, V. M., et al., "Coordination Ability of Amino-Acid Oximes—Potentiometric, Spectroscopic and Structural Studies of Complexes of 2-Cyano-2-(hydroxyimino)acetamide", *J. Chem. Soc. Dalton Trans.*, 273-276, (1997); and Sliva, T. Y.; Dobosz, A.; Jerzykiewicz, L.; Karaczyn, A.; Moreeuw, A. M., et al., "Copper(II) and Nickel(II) Complexes with Some Oxime Analogs of Amino Acids—Potentiometric, Spectroscopic and X-ray Studies of Complexes with 2-Cyano-2-(hydroxyimino)acetic acid and its Ethane-1,2-diamine Derivative", *J. Chem. Soc., Dalton Trans.*, 1863-1867, (1998)).

Recently, it has been recognized that α-(hydroxyimino)phosphonoacetic acids (also called phosphonoglyoxylic acid oximes, "α,α-disubstituted trifunctional oximes", or "Troika acids") are useful as pH-sensitive chelating agents. See, e.g., U.S. Pat. No. 5,948,931 to McKenna and Kashemirov, incorporated herein by reference in its entirety. Troika acids are molecules in which all of three potential metal coordinating groups—phosphonate, oxime and carboxylate moieties—are anchored to a common (α) carbon atom. Thus, Troika acids have three powerful functional groups that can coordinate heavy metal ions: a phosphonic acid group, $P(=O)(OH)_2$ (phosphonate when ionized); an oxime group, $=N-OH$; and a carboxylic acid group, $C(=O)(OH)$ (carboxylate when ionized); all of which are attached to an anchoring central carbon atom and each of which is ionizable according to ambient pH (see, Kashemirov, B. A.; Ju, J.-Y.; Bau, R.; McKenna, C. E., "'Troika Acids': Synthesis, Structure and Fragmentation Pathways of Novel α-(Hydroxyimino)phosphonoacetic acids", *J. Am. Chem. Soc.*, 117, 7285-7286, (1995)). The three groups, phosphonic acid, oxime and carboxylic acid, are depicted from left to right in each of structures 2a and 2b.

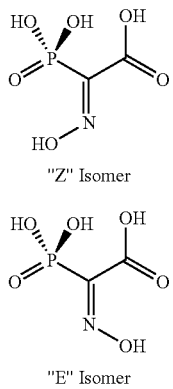

"Z" Isomer

"E" Isomer

An important feature of these compounds is that they have a tri-fold functionality, hence the name Troika.

Troika acids have unique properties not found in other chelating agents used in the art. For example, the mode of chelation for the Troika acids is different from common chelating agents such as ethylenediaminetetraacetic acid (EDTA). Specifically, a ligand such as EDTA coordinates a metal ion directly through an amine nitrogen atom, whereas a Troika acid coordinates through an oxime nitrogen atom.

Additionally, by virtue of its unique central location in the Troika acid structure, the oxime OH group can hydrogen-bond with either of its two neighboring groups, giving rise to two isomeric configurations, (E or Z), according to the particular conditions (see, e.g., Kashemirov, et al., *J. Am. Chem. Soc.*, 117, 7285-7286, (1995)), as illustrated in structures 2a and 2b. The two isomers are designated "E" and "Z" based on the orientation of the N—OH in space. Each of the two isomers has different properties. Thus, the oxime hydroxyl group significantly influences, if not directs, the chemical reactivity of either of its two neighboring groups, depending upon its position.

Furthermore, not only are Troika acids capable of strong metal complexation under specific conditions, but they can be designed to release the chelated cations through changes in condition, such as pH. However, if Troika acids are to find application in ion exchange, and, in particular to the sequestration of heavy metal ions found in effluents such as those from power-plants, ways must be found to incorporate them into the stationary phases of ion exchange apparatuses.

The discussion of the background to the invention herein is included to explain the context of the invention. This is not to be taken as an admission that any of the material referred to was published, known, or part of the common general knowledge at the priority date of any of the claims.

In addition, throughout the description and claims of the specification, use of the word "comprise" and variations thereof, such as "comprising" and "comprises", is not intended to exclude other additives, components, or steps.

SUMMARY OF THE INVENTION

The present invention describes novel ion-exchange materials that comprise a resin chemically linked to one or more α-hydroxyiminophosphonoacetate ("Troika") acids, and methods of preparing the same. Such ion-exchange materials are useful for selective chelation of heavy metal cations, particularly those found in industrial wastewaters, such as nickel (II), copper (II), mercury (II), or zinc (II). In one embodiment the resin is a microporous resin. In a preferred embodiment, the resin is a macroporous resin.

The present invention further encompasses methods of attaching a Troika acid to ion exchange beads or resins (including those that are commercially available), or to other substrates, through one of its three coordinating groups (carboxylate, phosphonate, or oxime), though it is preferred that the Troika acid is attached through either its carboxylate or its phosphonate group. For example, many different moieties can replace the terminal (OH) group found in each of the three Troika acid functional groups. In addition, a number of spacer groups can interpose between the Troika acid and the resin, lending somewhat different properties to the derivatized resin structure.

The present invention includes an ion exchange apparatus comprising: a macroporous resin; and, attached to the resin a ligand having a structural formula:

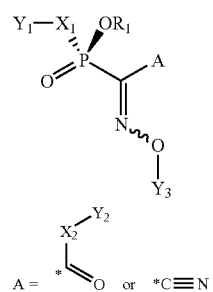

wherein: a starred atom denotes a point of attachment; N~O denotes a bond that represents the Z or E isomeric form; $X_1$ and $X_2$ are independently selected from the group consisting of: O, $NR_4$, and S; $Y_1$, $Y_2$, $Y_3$, $R_1$, and $R_4$ are independently selected from the group consisting of: hydrogen, alkyl, aryl, substituted alkyl, and substituted aryl; one of $Y_1$, $Y_2$, and $Y_3$ is absent so that respective group $X_1$, $X_2$, or $X_3$ to which it is bonded is attached directly to the resin, or one of $Y_1$, $Y_2$, and $Y_3$ is attached to said resin and is selected from the group consisting of: alkylene, oxy-alkylene, amino-alkylene, thio-alkylene, $-(CH_2)_nC(=O)NH-$, $-(CH_2)_nC(=O)O-$, arylene, substituted arylene, heteroarylene, and substituted heteroarylene; at least one of $R_1$, $Y_1$, $Y_2$, $R_4$, and $Y_3$ is hydrogen; and at least one of $R_1$ and $Y_1$ is not hydrogen.

The present invention also includes an ion exchange apparatus comprising: a macroporous resin; and, attached to the resin a ligand having a structural formula:

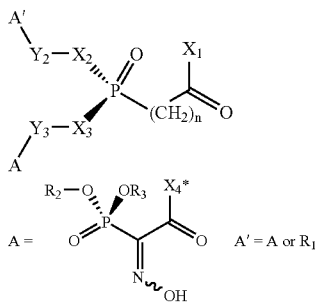

wherein: a starred atom denotes a point of attachment; N~O denotes a bond that represents the Z or E isomeric form; $X_1$, $X_2$, $X_3$ and $X_4$ are independently selected from the group consisting of: O, $NR_4$, and S; $X_1$ is attached directly to the resin; $Y_2$ and $Y_3$ are independently selected from the group consisting of: alkylene, oxy-alkylene, amino-alkylene, thio-alkylene, arylene, substituted arylene, heteroarylene, and substituted heteroarylene; $R_1$, $R_2$ and $R_3$ are independently selected from the group consisting of: hydrogen, alkyl, aryl, substituted alkyl, and substituted aryl; n is from 1 to 5; and, when n=1, the methylene group can be derivatized to form an imino group. Accordingly such a compound may comprise as many as 3 core Troika functionalities.

The present invention also comprises a compound of formula:

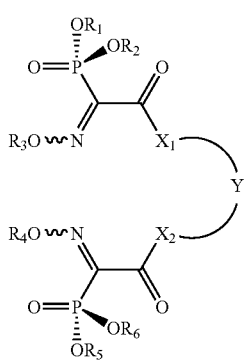

wherein $R_1$, $R_2$, $R_3$, $R_4$, $R_5$, and $R_6$ are selected from the group consisting of hydrogen, alkyl, aryl, substituted alkyl, and substituted aryl; at least one of $R_1$ and $R_2$ is not hydrogen; at least one of $R_5$, and $R_6$ is not hydrogen; $X_1$ and $X_2$ are each independently selected from the group consisting of O, $NR_7$, and S, wherein $R_7$ is hydrogen, alkyl, aryl, substituted alkyl, or substituted aryl; and Y is a linking group selected from the group consisting of: alkylene, substituted alkylene, alkylidene, substituted alkylidene, arylene, or substituted arylene. Such a compound may also be attached to a microporous or macroporous resin by methods described herein.

The present invention still further comprises a compound of formula:

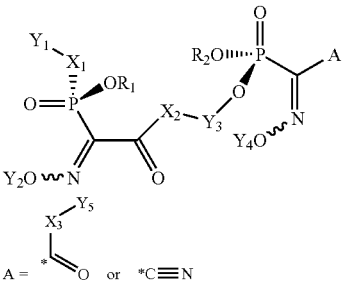

wherein: a starred atom denotes a point of attachment; $X_1$, $X_2$ and $X_3$ are independently selected from the group consisting of: O, $NR_3$, and S; $R_1$, $R_2$, $Y_1$, $Y_2$, $Y_3$, $Y_4$, and $Y_5$, are independently selected from the group consisting of hydrogen, alkyl, aryl, substituted alkyl, and substituted aryl; one of $Y_1$, $Y_2$, and $Y_3$ is selected from the group consisting of: alkylene, oxy-alkylene, amino-alkylene, thio-alkylene, $-(CH_2)_nC(=O)NH-$, $-(CH_2)_nC(=O)O-$, arylene, substituted arylene, heteroarylene, and substituted heteroarylene; at least one of $R_1$ and $Y_1$ is not hydrogen; and at least one of $R_1$, $R_2$, $Y_1$, $Y_2$, $Y_4$, and $Y_5$ is hydrogen; and at least one of $R_1$ and $Y_1$ is not hydrogen. Such a compound may also be attached to a microporous or macroporous resin by methods described herein.

The present invention comprises a ligand attached to a glass fiber, a silicon substrate, or a mesoporous phase, wherein the ligand has structure:

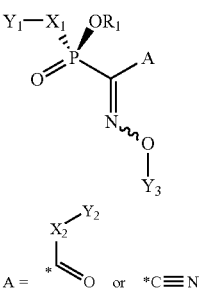

wherein: a starred atom denotes a point of attachment; N~O denotes a bond that represents the Z or E isomeric form; $X_1$ and $X_2$ are independently selected from the group consisting of: O, $NR_4$, and S; $Y_1$, $Y_2$, and $Y_3$, $R_1$, and $R_4$ are independently selected from the group consisting of: hydrogen, alkyl, aryl, substituted alkyl, and substituted aryl; one of $Y_1$, $Y_2$, and $Y_3$ is absent so that the respective group $X_1$, $X_2$, or $X_3$ to which it is bonded is attached directly to the resin, or one of $Y_1$, $Y_2$, and $Y_3$ attaches the ligand to the resin and is selected from the group consisting of: alkylene, oxy-alkylene, amino-alkylene, thio-alkylene, $-(CH_2)_nC(=O)NH-$, $-(CH_2)_nC$ (=O)O—, arylene, substituted arylene, heteroarylene, and substituted heteroarylene; at least one of $R_1$, $Y_1$, $Y_2$, $R_4$, and $Y_3$ is hydrogen; and at least one of $R_1$ and $Y_1$ is not hydrogen.

The present invention still further includes a method of removing metal cations from an aqueous medium, comprising: passing the aqueous medium over a macroporous resin, attached to which is a ligand of structure:

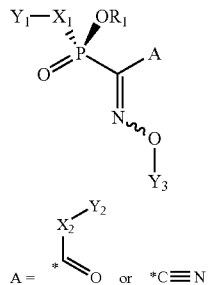

wherein: a starred atom denotes a point of attachment; N~O denotes a bond that represents the Z or E isomeric form; $X_1$ and $X_2$ are independently selected from the group consisting of: O, $NR_4$, and S; $Y_1$, $Y_2$, and $Y_3$, $R_1$, and $R_4$ are independently selected from the group consisting of: hydrogen, alkyl, aryl, substituted alkyl, and substituted aryl; one of $Y_1$, $Y_2$, and $Y_3$ is absent so that respective group $X_1$, $X_2$, or $X_3$ to which it is bonded is attached directly to the resin, or one of $Y_1$, $Y_2$, and $Y_3$ attaches the ligand to the resin and is selected from the group consisting of: alkylene, oxy-alkylene, amino-alkylene, thio-alkylene, —$(CH_2)_n$C(=O)NH—, —$(CH_2)_n$C(=O)O—, arylene, substituted arylene, heteroarylene, and substituted heteroarylene; at least one of $R_1$, $Y_1$, $Y_2$, $R_4$, and $Y_3$ is hydrogen; and at least one of $R_1$ and $Y_1$ is not hydrogen.

The present invention also encompasses use of any of the aforementioned ion exchange materials for sequestering heavy metal cations from aqueous media, in particular power plant discharge streams.

DETAILED DESCRIPTION

Figure 1:
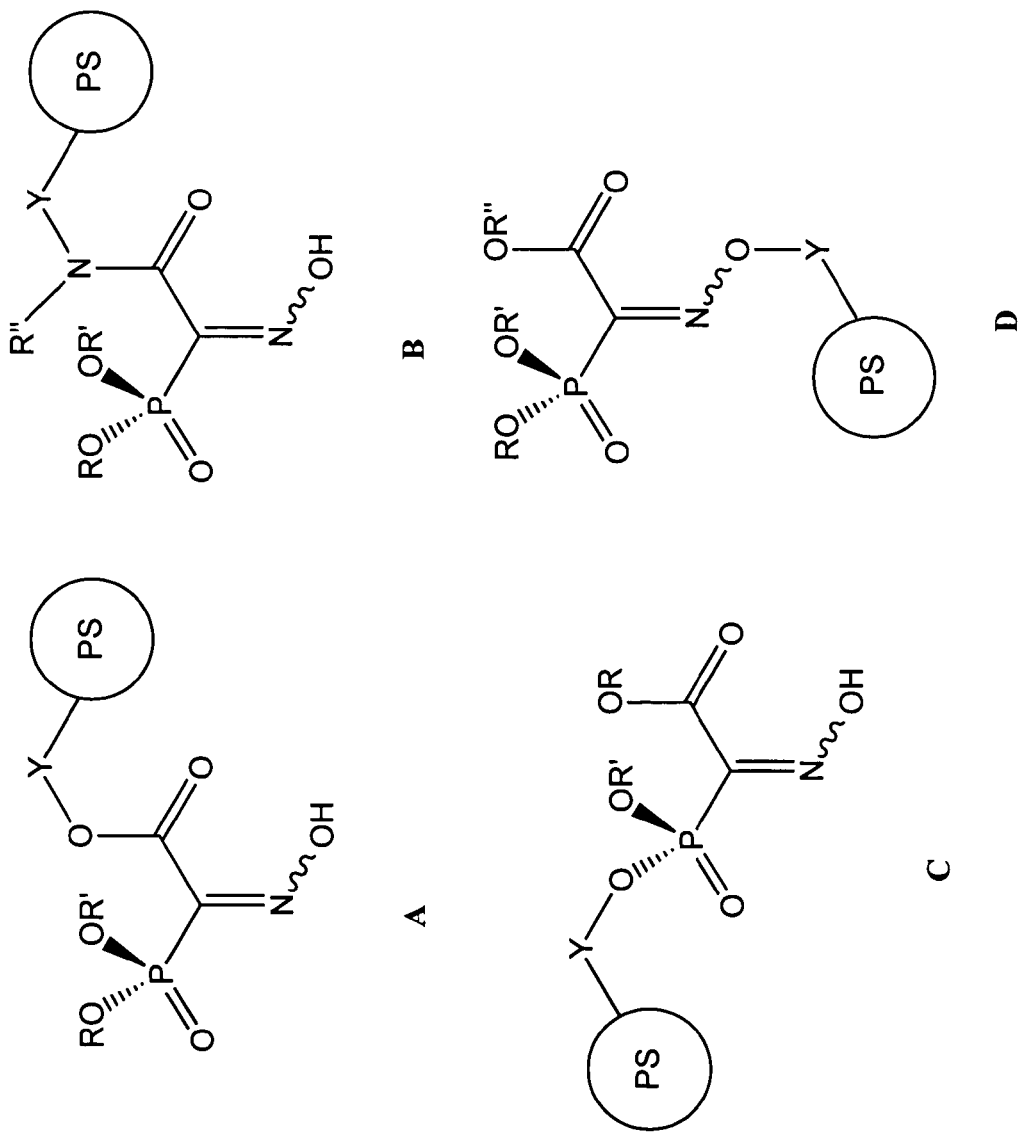
FIG. 1 depicts four alternate modes, denoted A, B, C, and D, of Troika acid attachment to a resin (circled "PS" in FIG. 1 and subsequent figures) wherein R, R', R" are groups further discussed herein, and Y is a spacer of a type that is further discussed herein.

The present invention generally provides novel ion-exchange materials that comprise a resin, including either a microporous or a macroporous resin, chemically linked to one or more α-hydroxyiminophosphonoacetate ("Troika") acids or derivatives thereof, including novel forms of the Troika acids and derivatives thereof, for use in ion exchange processes. The present invention also provides methods of preparing these ion-exchange materials.

Such ion-exchange materials are useful in the removal of heavy metal cations from liquid streams. For example, the ion-exchange materials of the present invention may be used in the removal of the heavy metal ions nickel (II), copper (II), mercury (II), and zinc (II) from industrial wastewaters. Such heavy metals are removed from liquid streams by chelation with the ion-exchange materials of the present invention.

Troika Acids

Troika acids may themselves be synthesized by methods known to an organic chemist, in particular by the methods described in U.S. Pat. No. 5,948,931, to McKenna et al., and in McKenna, et al., *J. Am. Chem. Soc.*, 117:7285-7286, (1995) including supplemental material entitled "Synthetic Procedures and Spectroscopic Data", available from the American Chemical Society, all of which are incorporated herein by reference in their entirety. Troika acids have three potential metal coordinating groups—phosphonate, oxime and carboxylate moieties—that are anchored to a common (α) carbon atom. Thus, Troika acids have three powerful functional groups that can individually coordinate heavy metal ions: a phosphonic acid group, P(=O)(OH)$_2$ phosphonate when ionized; an "oxime" group, =N—OH; and a carboxylic acid group, C(=O)(OH) (carboxylate when ionized); all of which are attached to an anchoring central carbon atom. As discussed further hereinbelow, these three functional groups provide the ability to attach a Troika acid to an ion-exchange resin using any one of these groups, as well as the ability to chelate heavy metals.

There are other advantages of using a Troika acid as a chelating agent. For example, the central oxime function can participate in bidentate metal ion coordination with either the phosphonic acid or the carboxylic acid group, depending on features of the particular Troika acid isomer used, thereby providing multiple modes of complexation to accommodate different types of metal ions. The presence of up to three ionizable groups in an immobilized Troika acid allows effective operation of the system over a relatively wide pH range near neutrality, while permitting regeneration under relatively mild acidic conditions. Thus, the Troika acid can be used under one set of pH conditions to complex a metal ion and under a second set of pH conditions to release the metal ion, thereby regenerating the Troika acid.

Troika Acid Derivatives

As noted, Troika acids have three functional groups that provide potential sites of derivatization. Such derivatives may be synthesized to facilitate attachment to a solid support, for example by using a spacer between the Troika acid and a resin, and to facilitate metal complexation. Troika acid derivatives may be synthesized according to methods described in U.S. Pat. No. 5,948,931, to McKenna et al., in McKenna, et al., *J. Am. Chem. Soc.*, 117: 7285-7286, (1995) including supplemental material entitled "Synthetic Procedures and Spectroscopic Data", available from the American Chemical Society, and in Carrick, J., Ph.D. Thesis, "Novel Troika Acid derivatives: Photochemistry and Metal Chelation", particularly chapters 2 and 3, University of Southern California, 2000, all of which are incorporated herein by reference in their entirety.

In general, the Troika functional group through which the Troika acid connects to a resin, either directly or indirectly, is referred to herein as a linking or linkage group. Even if the group is derivatized, e.g., carboxylic acid to amide, the group is still referred to in this way. If a further group interposes between the linking group and the resin, it is referred to as a spacer group. The term spacer is used herein whether or not such a group is bound to the resin, and thus encompasses both a group that is attached at one end to a Troika functional group and at its other end to the resin, as well as a group that is only attached at one such end prior to attachment to the resin.

Generally, preferred Troika acid derivatives for use with the present invention comprise compounds in which a hydroxyl group on one or more of the phosphono, oxime or carboxylate groups is substituted, or compounds in which such a hydroxyl group has exchanged a proton for another group. An example of the former would be a Troika acid amide formed by replacing the carboxylic acid OH group with an —$NH_2$ group. An example of the latter is a Troika acid ester formed by, say, alkylating the carboxylate group ("C-ester") or alkylating a hydroxyl group of the phosphonate group ("P-ester"). Compounds in which the oxime OH proton is exchanged are referred to as "NO-ethers".

A Troika acid derivative used with the present invention may be considered to be a Troika acid in which one or more of its functional groups is derivatized and, optionally, a spacer group is bound to a derivatized functional group. The spacer group is ultimately also attached to a solid support. Accordingly, preferred Troika acid derivatives for use with the present invention include Troika acids in which one or more of the three functional groups is derivatized with one of the following substituents: RO—, ArO—, Ar($CH_2$)$_n$O— with n=1-10, preferably n=1-5 but even more preferably n=1, R'NH—, ArNH—, Ar($CH_2$)$_n$NH— with n=1-10, preferably n=1-5 but even more preferably n=1, and RC(=O)O—, wherein: R is alkyl, alkenyl, alkynyl; R' is hydrogen, alkyl, alkenyl, alkynyl; Ar is aryl, which includes, but is not limited to, phenyl, naphthyl, anthracyl, and phenanthryl. It is further to be understood that R and R' (other than hydrogen) may also be substituted with one or more functional groups selected from the group consisting of: halide (comprising, preferably, F, Cl, Br, and I); hydroxy; alkoxy; nitro; sulfoxy; amino; thio; cyano; carboxy; and phosphoryl.

Troika acid C-esters provide models for metal chelating materials in which a Troika acid is covalently immobilized on a water-insoluble resin bead via a C-esteric [C(=O)O—] or C-amido [C(=O)N(H)—] linkage. Similar linkages via the phosphonate group are also consistent with the present invention. A P-ester provides a model for novel metal chelating materials in which a Troika acid is covalently immobilized on a water-insoluble resin bead via a P-monoesteric [P(=O)O—] or P-amido [P(=O)N(H)—] linkage. A third model for immobilization of a Troika acid is to create an ether-type linkage between the oxime =N—OH group and the supporting resin (i.e., =N—OR), though these are less preferred.

In one embodiment of the present invention, modifications to the Troika acid α-carboxyl group permit modulation of the hydroxyiminophosphonate moiety's reactivity. For example, chemical or enzymatic unmasking of a neutral Troika acid carboxyl derivative such as a C-ester to generate the free carboxylic acid (or carboxylate anion), significantly modifies the interaction between the carboxyl moiety and the oxime hydroxy (as well as, possibly, the phosphonate) groups. Such a process can be referred to as C-group dependent P-activation. In practice, such a process can also be mediated by a reagent or catalyst that is highly specific for the C-moiety.

The carboxyl function also profoundly influences the chemical properties of Troika acids. As noted hereinabove (see, e.g., E. Breuer, *Acylphosphonates and their Derivatives*, John Wiley & Sons, 1996), simple bifunctional α-hydroxyimino phosphonic acids (diacids) are unstable in aqueous solution, and hence do not make suitable metal complexing agents (see also, e.g., Breuer, et al., *J. Chem. Soc. Chem. Commun.*, 671-672, (1987); Breuer, et al., *J. Chem. Soc. Chem. Commun.*, 504-506, (1988); Breuer, et al., *J. Org Chem.*, 56:4791-4793, (1991); and Mahajna, et al., *J. Org. Chem.*, 58:7822-7826, (1993)). However, C-esters (or C-amides) of Troika acids are quite stable near neutral pH at room temperature.

Certain derivatives illustrate a unique property of Troika acids, referred to as the "stability switch". Although C- and P-esters of a parent Troika acid are stable in water near neutral pH's, the Troika acid itself undergoes fragmentation under such conditions. As a result, reagent-specific esterolytic cleavage of an appropriately designed C- or P-ester leads to decomposition of the resulting Troika acid. The fragmentation is stereospecific to each of the two E or Z isomeric forms, giving respectively phosphate or phosphorocyanidate species. This principle has been demonstrated by saponification of the E or Z C-methyl esters with strong alkali, followed by neutralization of the solution, a procedure which induced decomposition of both isomers (see, e.g., Kashemirov, et al., *J. Am. Chem. Soc.*, 117:7285-7286, (1995)).

With some derivatives, the stability switch can be turned 'off' or caused to be shifted to different pH ranges. In one embodiment, if a photosensitive o-nitrobenzyl ester group is used instead of a methyl ester group, decomposition can be induced under very mild conditions by exposure of the compound to UV light (see Carrick, J. M.; Kashemirov, B. A.; McKenna, C. E., "Indirect Photo-Induced Phosphorylation via a C-Ester Caged Troika Acid", *Phosphorus, Sulfur and Silicon*, 147, 65, (1999); Carrick, J. M.; Kashemirov, B. A.; McKenna, C. E., "Indirect Photo-Induced Phosphorylation via a photolabile troika acid C-ester: o-nitrobenzyl (E)-(hydroxyimino)-(dihydroxyphosphinyl)acetate", *Tetrahedron*, 56:2391-2396, (2000)). In another embodiment, use of a group such as the p-nitrophenyl group, that is much more susceptible to hydrolysis than the methyl ester group, produces a Troika acid C-ester that can be decomposed under moderately alkaline conditions. When such compounds are complexed with $Ni^{2+}$ ions, decomposition is accelerated nearly a thousand-fold when the pH is increased from 5 to about 8, whereas simple alkyl esters are stable over such a range of conditions. (For a description of use of the p-nitrophenyl group, see, e.g., Kashemirov, B. A.; Fujimoto-Posner, M.; McKenna, C. E., "Effects of divalent Metal Ions on pH-Dependent Hydrolysis of p-Nitrophenyl (E)-(Hydroxyimino)-phosphonoacetate", Phosphorus, Sulfur and Silicon, 147, 153, (1999)).

Troika acid functional groups can also be modified to increase the affinity of the Troika acid for certain specific substances, such as mercury and its compounds. Mercury recovery is a useful application for Troika acids because the Troika acid is easily decomposed in a manner that releases the bound atoms (for methods, see, for example, Kashemirov, B. A., et al., J. Am. Chem. Soc., 117, 7285-7286, (1995)). Mercury recovery from the capturing matrix is therefore feasible, allowing opportunities for mercury recovery or disposal without contamination from the supporting substrate.

Attaching Troika Acids to Solid Supports

Troika acids can bind to both macroporous and microporous resins, thus permitting them to work function in both aqueous and non-aqueous environments, respectively. The active part of the Troika acid that chelates a metal cation can be made hydrophilic while the attachment side can remain hydrophobic. Such a "hybrid" structure is capable of, for example, capturing ions from an aqueous solution, which can later be released into a non-aqueous solvent. This feature has application to treatment of aqueous solutions with high organic concentrations, such as waste from coal or other fuel gasification applications. This feature may also have application to mining operations, specifically as a step in solvent based extractions of valuable metals.

As noted, the Troika acids and derivatives thereof may be used with either microporous or macroporous ion-exchange resins. Although macroporous and microporous resins are both composed of insoluble polymers (such as PS-DVB), a macroporous resin differs from a microporous resin in that it has a larger pore size and a greater degree of cross-linking. Consequently, a macroporous resin can accommodate more solvent molecules, and larger solute molecules, than can a microporous resin. It is found that, whereas a microporous resin typically has around 1% cross-linking, a macroporous resin typically has at least about 10% cross-linking. Accordingly, preferred macroporous resins for use with the present invention preferably have from about 5% to about 20% cross-linking, more preferably about 5% to about 15% cross-linking, and even more preferably, from about 5% to about 8%, or from about 8% to about 12% cross-linking. Additionally, preferred macroporous resins for use with the present invention have pore sizes in the range of 100-300 μm, preferably 150-300 μm, and more preferably, 150-250 μm. Furthermore, macroporous resins for use with the present invention have mesh sizes in the range 50-200 mesh, preferably 100-200 mesh, and even more preferably 50-100 mesh.

Macroporous resins suitable for use with the present invention include those resins that are used in various water treatment and industrial processing applications, such as polyamine, amine-modified styrene-divinylbenzene, aminated phenol-formaldehyde, or amine-modified acrylic resin types. The acrylic resins are also called "polyacrylic macroporous" resins Such resins may be available from the Dow Chemical company, and include Diethylenetriamine (DETA); Triethylenetetramine (TETA); and Tetraethylenepentamine (TEPA). A preferred macroporous resin for use with the present invention is polystyrene-divinylbenzene (PS-DVB), which can be obtained commercially. This PS-DVB resin has a number of advantageous properties: it has a higher level of cross-linking (8% vs. 5%); and it offers better swelling in organic solvents. Other commercially available macroporous resins may be satisfactorily attached to Troika acids.

PS-DVB resins whose cross-linking is more than 5% become rigid and do not produce gels in organic solvents, so their reactivity in organic solvents is often diminished relative to that of microporous resins. Accordingly, reaction conditions found to be suitable for derivatizing and deploying microporous resins cannot be expected to be suitable for macroporous resins. Thus, reaction conditions found suitable for attaching a Troika acid to a microporous resin require modification before they can be applied to preparation of the corresponding macroporous Troika acid resin, as is further discussed herein.

As noted, a great advantage of a Troika acid lies in its chemical versatility: it offers three potential sites for immobilization (see FIG. 1) as well as via derivatives of such sites such as modified functional groups with or without interposition of a spacer moiety, thereby providing flexibility in design. At two of these sites, phosphonate (C in FIG. 1) and carboxylate (A in FIG. 1), a variety of linkages is possible. In each case, a suitable spacer (Y in FIG. 1) may be interposed between the support and the functional group. At the oxime site (D in FIG. 1), linkages are less preferred.

Accordingly, the present invention includes an ion exchange apparatus that comprises: a resin; and, attached to the resin a ligand having a structural formula:

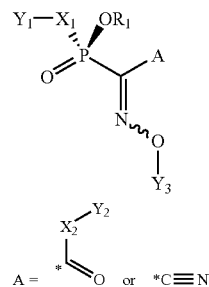

wherein: a starred atom denotes a point of attachment; N~O denotes a bond that represents the Z or E isomeric form; $X_1$ and $X_2$ are independently selected from the group consisting of: O, $NR_4$, and S; $Y_1, Y_2, Y_3, R_1$, and $R_4$ are independently selected from the group consisting of: hydrogen, alkyl, aryl, substituted alkyl, substituted aryl, and any other suitable spacer group described herein; one of $Y_1, Y_2$, and $Y_3$ is absent so that the respective group $X_1, X_2$, or $X_3$ to which it is bonded is attached directly to the resin, or one of $Y_1, Y_2$, and $Y_3$ is attached to the resin and is selected from the group consisting of: alkylene, oxy-alkylene, amino-alkylene, thio-alkylene, —$(CH_2)_nC(=O)NH$—, —$(CH_2)_nC(=O)O$—, arylene, substituted arylene, heteroarylene, substituted heteroarylene, and any other suitable spacer group described herein; at least one of $R_1, Y_1, Y_2, R_4$, and $Y_3$ is hydrogen; and at least one of $R_1$ and $Y_1$ is not hydrogen.

Linkages that are suitable for attachment to a solid support include, but are not limited to: ester linkages and amide linkages, attached to which is optionally a suitable spacer interposed between the ligand and the resin. In particular, an amide (—C(O)NH—) linkage is a more stable alternative to an ester (—C(O)O—) linkage, which would have poor resistance to very strong acids that are typically used in the art to regenerate cation exchange resins. Despite the fact that much milder regeneration conditions are possible with Troika acids, resistance to acid is a desirable trait of any linkage.

Figure 2:
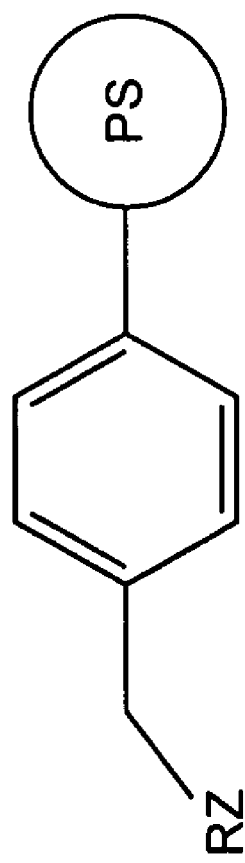
FIG. 2 depicts exemplary polar spacer groups attached to a resin such as PS-DVB that are suitable for joining a Troika acid to a polymer bead.

Accordingly, a preferred method of attachment to a macroporous or microporous resin is via a carboxamide (amide) linkage. In particular, a carboxamide linkage may be derived from an amino-derivatized polymer support, such as a polystyrene-divinyl benzene polymer in particle or bead form. An exemplary chelator resin support material is aminomethyl polystyrene (AMPS). Examples of derivatized resins that provide such linkages with variable spacers are shown in FIG. 2.

Spacer groups include, but are not limited to, the following: alkylene, $-(CH_2)_n-$, preferably methylene ($-CH_2-$), more preferably with n=1-10, even more preferably with n=1-5; oxy-alkylene, such as $-(CH_2)_nO-$, with n=1-10, preferably n=1-5; amino-alkylene, such as $-(CH_2)_nNH-$, with n=1-10, preferably n=1-5; thio-alkylene, such as $-(CH_2)_nS-$, with n=1-10, preferably 1-5; amides such as $-(CH_2)_nC(=O)NH-$; esters such as $-(CH_2)_nC(=O)O-$; arylene such as phenylene ($-C_6H_4-$), naphthylene, anthracenylene, and phenanthrylene, and substituted forms thereof; and heteroarylenes such as furylene, pyrrolidene, pyridinyl, indyl, and substituted forms of any of the foregoing heteroarylenes. It is to be understood that, in the foregoing list of spacers, as with elsewhere herein, a designation such as $-(CH_2)_n-$ is to be taken to also include isomeric branched forms thereof. For example, in the case of n=3: the list includes $-CH(CH_3)CH_2-$ as well as the unbranched form, $-CH_2CH_2CH_2-$. It is further to be understood that when referring to a substituted form of a spacer group in the foregoing list as with elsewhere herein, the substituents in question may include, but are not limited to, moieties selected from the group consisting of: alkyl, including branched alkyl, preferably with 1-5 carbon atoms; alkenyl; alkynyl; aryl, preferably phenyl; heteroaryl; hydroxyl; alkoxy, such as methoxy; amino; alkyl amino; nitro; cyanyl; sulphoxy; halide; and phosphoryl. It is further to be understood that substitutents such as alkyl, alkenyl, alkynyl, aryl, and heteroaryl, may also themselves be further substituted by substituents from the same list. For example, then, a substituent on a spacer group such as phenylene, may be a halo-alkyl group such as trifluoromethyl. Such substituents may be introduced by methods familiar to one of ordinary skill in the art. In general, it is preferred that such spacers are not too hydrophobic so that the Troika acids can be effectively solubilized in an aqueous medium.

It is to be noted that it is consistent with the present invention that a spacer group is first attached to the resin, for example during derivatization of the resin, and is then attached to the linking group on the Troika acid. It is also possible that a Troika acid is first derivatized in such a manner that a spacer group is attached to a linking group, and thereafter the assembly is joined to the resin via the free end of the spacer group.

It will be appreciated by those of ordinary skill in the art that any of the Troika acid resin materials described herein including multi-Troika acids bound to a resin, the spacer length and polarity may advantageously be varied to achieve optimal metal chelating resin performance. By so modifying the length and chemical structure of the spacer, fine tuning of metal complexation properties is possible.

Figure 3:
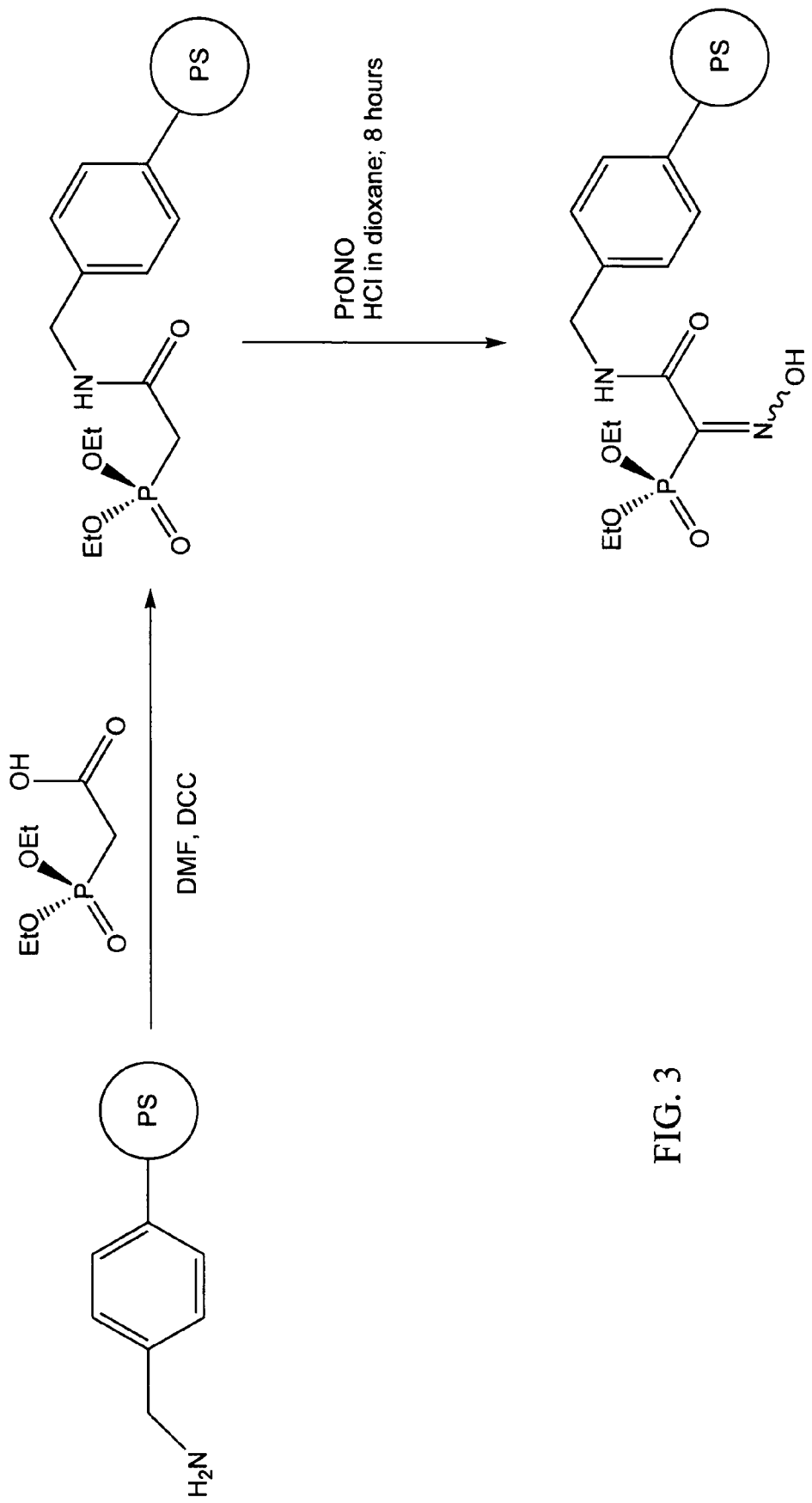
FIG. 3 depicts a scheme to synthesize an exemplary mono-Troika acid-modified resin, which has a benzyl-carboxamide link, wherein the depicted benzene ring is part of a styrene unit in the resin so that the circled "PS" moiety represents the polymer backbone and other pendant phenyl groups, and wherein a Troika acid precursor is reacted with a derivatized resin and the Troika acid is generated in situ.

In general, a Troika acid may be attached to a resin in one of two preferred ways. It is to be understood that other methods of attachment may be applicable. In one approach, a Troika acid precursor such as an α-phosphono-acetic acid is attached to a polymer support. The bound Troika acid is then formed in situ by derivatizing the precursor. An exemplary embodiment in which the ligand is constructed on a methylene-aminated resin after attachment of a diethyl phosphonacetic acid precursor is shown in FIG. 3. Such a method may be generalized to other precursors of other Troika acids described herein. Accordingly, a preferred embodiment of the present invention includes a method to couple dialkyl phosphonoacetic acid to an alkylene-aminated resin, and also conditions for incorporating an oxime group after immobilization, using a nitrosation procedure, thereby resulting in a Troika acid bound to a macroporous resin. In FIG. 3, and in subsequent figures, the depicted phenyl group is sidechain of a styrene unit in a polymer molecule of the resin. The backbone of the polymer molecule is not explicitly shown.

Figure 4:
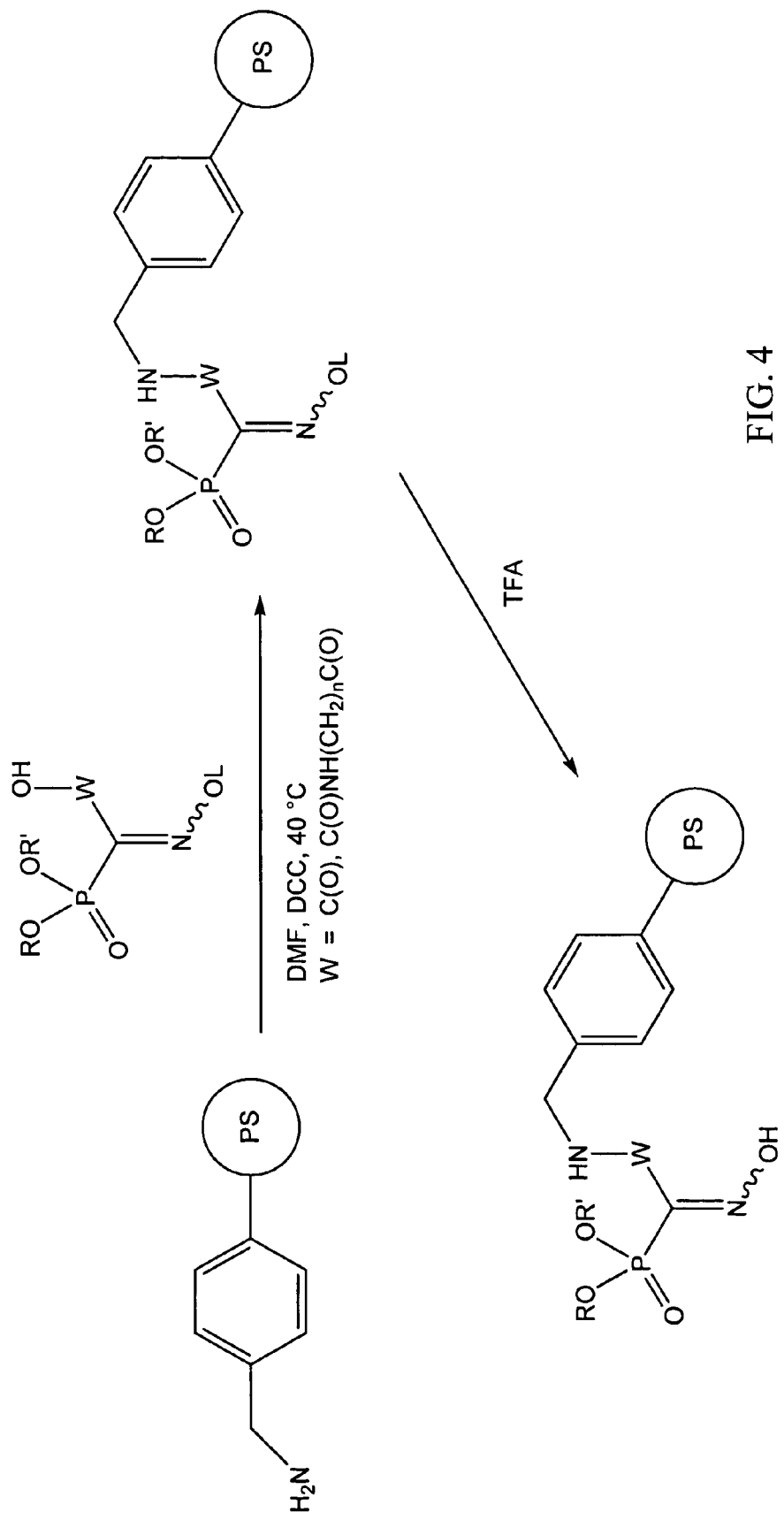
FIG. 4 depicts an alternative method of preparing a mono-Troika acid-modified resin having a benzyl-carboxamide link in which a preformed Troika acid with a suitable protecting group L is directly attached to a functionalized resin.

In a second approach, in appropriately tuned conditions, preferably using a mixture of DMF and the coupling agent dicyclohexylcarbodiimide (DCC) at a temperature of 40° C., a preformed Troika acid or Troika acid ester is reacted directly with a support. An exemplary embodiment of such an approach is shown in FIG. 4. In a preferred embodiment of the species shown in FIG. 4, R, and R' are independently alkyl groups (e.g., Me, Et, Pr, i-Pr, Bu, t-Bu), W is a carbonyl, or substituted amide group (such as $C(=O)NH(CH_2)_nC(=O)$, preferably with n=1-10), and L is a protecting group such as trityl ("Tr"=$CPh_3$) that is employed on the oxime oxygen.

As would be understood by one of ordinary skill in the art, the conditions for effecting the coupling of a Troika ligand to a support may vary according to whether the Troika ligand already contains an oxime functionality or whether the oxime group is added after the molecule is bound to the support.

With either of the two approaches described hereinabove, the resin may be immediately suitable for attachment of a Troika acid precursor or Troika acid respectively. Alternatively, a resin may need to be initially derivatized before, respectively, a Troika acid precursor or Troika acid can be attached to it.

Appropriately derivatized resins are available commercially. It is preferable that resins for use with the present invention are purchased pre-derivatized. Preferably, the resin is derivatized to an amino functionality. Commercially available resin with chloromethyl functionality can also be converted to the desired amino functionality, utilizing the Gabriel reaction or other reactions known to one of ordinary skill in the art.

A preferred macroporous resin, PS-DVB, for use with the present invention is advantageous because it is available in the aminomethyl, not chloromethyl, form thereby saving one synthetic step in forming a Troika acid-bound resin.

Since commercially available ion exchange resins can be functionalized with Troika acids and, in bead form, the functionalized form can be used to chelate heavy metal cations, the ion-exchange materials of the present invention may be used in conjunction with common ion exchange resin beads in many types of water and wastewater treatment equipment. Such an application is advantageous because it can be deployed within existing wastewater treatment plants with minimal re-engineering and without extensive retraining of personnel.

A further advantage of the present invention is that Troika acids can be readily separated from an ion exchange resin and can thereby release their metal payload. Such a property can also be important for hazardous waste disposal because the resin beads can be physically separated from the hazard causing materials, thereby greatly reducing the mass and volume, and, therefore, the cost of disposal.

Troika acids can also be functionalized to attach to a variety of non-traditional substrates such as glass fibers, silicon substrates, and mesoporous powders. See, for example, "Polyamide-containing ligands covalently bonded to supports, polyamide-containing resins, and methods for removing metals from solutions", Bruening, R. L., and Krakowiak, K. E., PCT Publication No. WO 01/23067 A1, (2001).

Other examples of substrates for use with Troika acids of the present invention include: ion-exchange fibers that are prepared by coating low-cost glass fiber substrates with an appropriate oligomer (e.g., styrene di-vinyl benzene); crosslinking, and functionalizing the coating to produce either anionic or cationic capability. See, for example: L. Dominguez, Z. Yue, J. Economy, C. Mangun, "Design of polyvinyl alcohol mercaptyl fibers for arsenite chelation," *Reactive and Functional Polymers,* 53(2-3), 205-215, (2002); J. Economy, L. Dominguez, C. Mangun, "Polymeric ion exchange fibers," *Industrial and Eng. Chemistry Research,* 41(25), 6436-6442, (2002); and J. Economy, C. Mangun, "Novel fibrous systems for contaminant removal," in *Sampling and Sample Preparation for Field and Laboratory,* Ed. J. Pawliszyn, Elsevier Science, (2002), all of which are incorporated herein by reference in their entirety. Such materials remove most ionic contaminants to well below EPA standards and offer simplified synthesis relative to other resins; resistance to osmotic shock; very high selectivity for heavy metal cations such as $Hg^{2+}$, $Pb^{2+}$; and up to 10 times the increase in rate of reaction/regeneration. Ion-exchange fibers may be tailored to achieve selectivity in their exchange reactions, by altering their molecular architecture, for example by varying the size and functionality of the pendant molecules and inorganic groups. Examples of such selectivity include differentiating monovalent over divalent species. See, e.g., the internet web-site economy.mse.uiuc.edu/contact.htm.

Additionally, silicon and other semiconductor substrates are being manufactured as very thin wafers with multitudes of small tubes passing through the wafer, thereby creating a plethora of short passage microfilter tubes. The insides of the tubes are ripe for attaching Troika acids and lead to many different membrane/ion exchange hybrid applications. Such systems can have applications to metal extraction from both liquid and gas streams.

All of these materials are cheaper than resin beads and potentially offer much higher attachment surface area per unit mass of material.

Thus, the present invention additionally includes a ligand attached to a glass fiber, silicon substrate, or mesoporous phase, wherein the ligand has structure:

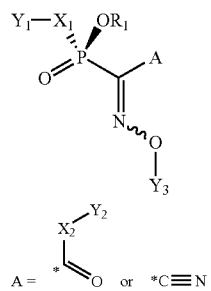

wherein: a starred atom denotes a point of attachment; N~O denotes a bond that represents the Z or E isomeric form; $X_1$ and $X_2$ are independently selected from the group consisting of: O, $NR_4$, and S; $Y_1$, $Y_2$, and $Y_3$, $R_1$, and $R_4$ are independently selected from the group consisting of: hydrogen, alkyl, aryl, substituted alkyl, substituted aryl, and any other suitable spacer group described herein; one of $Y_1$, $Y_2$, and $Y_3$ is absent so that respective group $X_1$, $X_2$, or $X_3$ to which it is bonded is attached directly to the resin, or one of $Y_1$, $Y_2$, and $Y_3$ attaches the ligand to the resin and is selected from the group consisting of: alkylene, oxy-alkylene, amino-alkylene, thio-alkylene, —$(CH_2)_nC(\!=\!O)NH$—, —$(CH_2)_nC(\!=\!O)O$—, arylene, substituted arylene, heteroarylene, substituted heteroarylene, and any other suitable spacer group described herein; at least one of $R_1$, $Y_1$, $Y_2$, $R_4$, and $Y_3$ is hydrogen; and at least one of $R_1$ and $Y_1$ is not hydrogen.

Such compositions find application to the removal and recovery of metal ions, in particular heavy metal ions, from solution, including waste solutions from industrial processes.

Metal Complexation

The Troika acids and Troika acid derivatives of the present invention preferentially chelate heavy metal cations. For the purposes of the present invention, a heavy metal is one whose atomic number is 19 or greater and is preferably an element found in the d-block of the periodic table (including both transition metals and those containing filled d-electron valence shells), although it may be a metal in the p-block of the periodic table. Much less preferred are heavy metals from the s-block of the periodic table. In addition, the present invention provides for Troika acid and Troika acid derivatives that are chelators for cations of f-block elements such as the lanthanides (cerium, samarium, etc.) and actinides (thorium, uranium, plutonium, etc.). With suitable modifications, the Troika acid compounds may also be applied to removal of ions derived from main group elements, whether metallic or semi-metallic, such as arsenic, lead, selenium, or bismuth.

Accordingly, Troika acids of the present invention preferably chelate metal cations selected from the group consisting of: d-block elements, f-block elements, and p-block metals with atomic number 31 and greater. More preferably, the Troika acids of the present invention selectively chelate cations of d-block and f-block elements. Even more preferably the Troika acids of the present invention selectively chelate cations of elements from the first row of the d-block. Yet more preferably, the Troika acids of the present invention selectively chelate cations of elements from the second and third rows of the d-block. Still more preferably, the Troika acids of the present invention selectively chelate cations of lanthanide, actinide and trans-uranic elements. Most preferably, the Troika acids of the present invention selectively chelate cations of elements selected from the group consisting of: nickel, cobalt, copper, mercury, cadmium, and zinc. The oxidation states of the metal cations that are selectively chelated by the Troika acids of the present invention are preferably those oxidation states that are most stable in aqueous solution. In particular, the Troika acids of the present invention preferably selectively chelate metal cations whose oxidation states are +1, +2, +3, +4, +5, and +6. Even more preferably the Troika acids selectively chelate metal cations whose oxidation states are +1, +2, or +3. Most preferably, the Troika acids of the present invention selectively chelate metal cations whose oxidation state is +2.

In connection with the present invention, Troika acids and their derivatives act as chelates by forming coordinate bonds between a pair of Troika acid heteroatoms and a metal cation. This means that, in practice, E-isomer Troika acids chelate a metal cation through an oxygen on the phosphonate (acid or ester) group and the oxime nitrogen atom. Correspondingly, Z-isomer Troika acids chelate a metal cation through a carboxylic acid oxygen atom and the oxime nitrogen atom. It is noted that in both of these modes, the configuration that comprises the metal cation, the two chelating atoms and the Troika acid backbone between them, is a 5-membered ring, which is a particularly stable arrangement. Which of the two chelating modes is favored may be altered by an appropriate derivatization of the Troika acid. In general, however, a Troika acid preferentially chelates a metal ion through the phosphonate and oxime groups, whether the Troika acid bonds to the resin through the phosphoric acid group or through the carboxylate group. Accordingly, the preferred mode of metal chelation exhibited by Troika acid P-monoester and Troika acid C-esters are illustrated by structure 3.

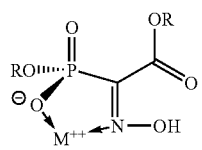

3

As discussed hereinabove, the carboxylic acid group primarily functions to alter the pH and to determine whether or not the oxime group is protonated. As would be understood by one of ordinary skill in the art, the oxime group may be protonated (as shown in structure 3) or not, according to pH.

The pKa of the oxime hydroxylproton is higher than that of the P—OH or C(O)—OH protons. Therefore, it will be appreciated by one of ordinary skill in the art that the oxime group can ionize near neutral to weakly acidic pH, thereby enhancing the Troika acid's complexation of cations. It will be further so appreciated that the oxime group thereby confers selectivity in heavy metal cation vs. alkaline earth or alkali cation binding because it provides stronger coordinating ability (through the oxime nitrogen atom) than does an —O— moiety. Accordingly, it is preferable to keep the Troika acid phosphonate group neutral or esterified.

The difference in mode of chelation can be readily appreciated from a visual comparison of the color of fully loaded resins. Conventional resin loaded with chelated copper is a bright blue, typical of cupric ($Cu^{2+}$) compounds, whereas Troika acid derivatized resins loaded with the same copper solutions are an avocado green color, characteristic of copper—oxime coordination complexes.

Another advantage is that Troika acids can release their chelated cations upon relatively mild changes in pH or by other specific reaction conditions. For example, cleavage of a Troika acid from a support and subsequent release of a cation can be triggered by exposure to light in certain configurations.

In addition to their metal chelating abilities, Troika acid derivatives provide unique mechanisms for metal release. A Troika acid has at least one uncommitted group (OH or NH) when two functional groups are committed to metal ion coordination in a complex and one is used to create a covalent linkage to a supporting resin. Additionally, the pKa of the oxime group of a Troika acid is lower than that of other oximes, due in part to the presence of the adjacent phosphoryl and carbonyl groups, and also in part to intramolecular H-bond stabilization of the oxime anion that is possible in some derivatives such as a Troika amide. There is an intramolecular hydrogen bond between amido-NH and oxime-O in a Troika amide, as has been confirmed by an X-ray structure of a nickel complex, discussed hereinbelow. Thus, Troika acids give better complexation due to involvement in the complex of not only the oxime nitrogen but also the oxime oxygen, as confirmed by X-ray structures. However, the pKa of the oxime hydroxylproton (~6-8 in Troika derivatives) is higher than that of the COOH proton (~5), as found, for example, in Chelex. The effect of pKa is that chelated ion is released under less acidic conditions. Therefore, there is a potentially narrower range of acid pH over which release of chelated ion can be achieved than with other chelating agents known in the art, and means that a wider variety of reagents (e.g., weak rather than strong or concentrated acids) may be acceptable for regeneration of a Troika resin. Accordingly, Troika acids provide improved control over metal affinity as a function of pH.

One advantage of the present invention is that the presence of alkali metal ions such as sodium and potassium, and alkaline earth metal ions such as calcium and magnesium, has little effect on the ability or capacity of the Troika acids to chelate heavy metals. This means that the Troika acids can function as heavy metal removers, even in the presence of high concentrations of other cations. Examples of applications in which such an advantage is important include: heavy metal removal from limestone-based flue-gas desulfurization (FGD) process water; removal of heavy metals from highly concentrated brines, such as cooling tower and evaporator blowdown; capture of heavy metals from less concentrated solutions such as coal pile runoff, ash sluicing water, and ash pond water; and removal of heavy metals from neutralized conventional ion exchange wastes. Such applications are extremely advantageous if the heavy metal content of the waste water, prior to treatment, is high enough to cause the waste water to be treated as a hazardous waste. Thus, removal of the offending metals can result in greatly reduced disposal costs of the high volume brines relative to the ion exchange materials that have been used hitherto. Further, the ability of Troika acids to strongly chelate ions of lanthanide and actinide series elements gives rise to applications to separate such ions from condensate and effluent from boiler recirculation water systems at nuclear power stations.

The metal-binding properties of the resin material of the present invention can be investigated by exposing it to an aqueous solution of a heavy metal ion, such as $Cu^{2+}$, stripping the bound metal from the resin using acid, and analyzing the recovered metal by flame atomic absorption spectroscopy (e.g., using a Perkin Elmer 2380 AAS spectrometer, P-E $Cu^{2+}$ lamp, $C_2H_2$-air flame).

Multiple Troika acids

The present invention further includes multiple Troika acids. In particular, the present invention also includes a ligand suitable for attaching to a macroporous resin, having a structural formula:

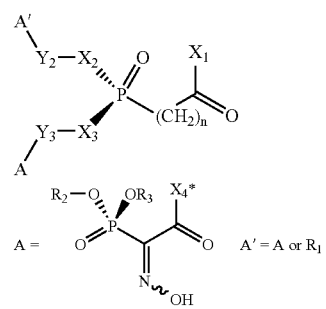

wherein: a starred atom denotes a point of attachment; N~O denotes a bond that represents the Z or E isomeric form; $X_1$, $X_2$, $X_3$ and $X_4$ are independently selected from the group consisting of: O, $NR_4$, and S; $X_1$ is attached directly to the resin; $Y_2$ and $Y_3$ are independently selected from the group consisting of: alkylene, oxy-alkylene, amino-alkylene, thio-alkylene, arylene, substituted arylene, heteroarylene, and substituted heteroarylene; $R_1$, $R_2$ and $R_3$ are independently selected from the group consisting of: hydrogen, alkyl, aryl, substituted alkyl, and substituted aryl; n is from 1 to 5; and, when n=1, the methylene group can be derivatized to form a hydroxy-imino group.

In preferred embodiments of the compound shown, $X_1$ and $X_4$ are both N(H) groups, $X_2$ and $X_3$ are both oxygen, $Y_2$ and $Y_3$ are both independently alkylene groups, $—(CH_2)_n—$ where n=1-5, and $R_1$, $R_2$, and $R_3$ are all lower alkyl such as methyl, ethyl, propyl, or butyl.

Such a compound can be characterized as a "multiple Troika acid" because it may comprise as many as 3 core Troika functionalities. Groups A and A' can both be obtained by attaching a Troika acid to the remainder of the molecule, thus giving a molecule with two Troika functionalities. Additionally, in the situation where n=1, the methylene group closest to the resin can be derivatized by methods described herein to form a hydroxy-imino group (—C=N—OH). In such a situation, a Troika derivative is bound to the resin in addition to whichever of groups A and A' are Troika derivatives.

These compounds can be synthesized by a combination of the methods described herein in addition to well-known techniques of organic chemistry, as would be understood by one of ordinary skill in the art, and, similarly, may be attached to a macroporous resin by any of the methods described herein.

The present invention further includes compounds whose structure comprises:

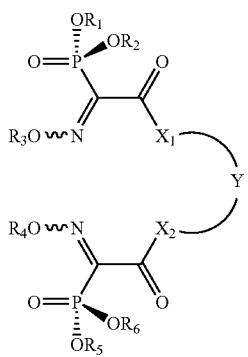

wherein $R_1$, $R_2$, $R_3$, $R_4$, $R_5$, and $R_6$ are selected from the group consisting of hydrogen, alkyl, aryl, substituted alkyl, and substituted aryl; at least one of $R_1$ and $R_2$ is not hydrogen; at least one of $R_5$, and $R_6$ is not hydrogen; $X_1$ and $X_2$ are each independently selected from the group consisting of O, $NR_7$, and S, wherein $R_7$ is hydrogen, alkyl, aryl, substituted alkyl, or substituted aryl; and Y is a linking group selected from the group consisting of: alkylene, substituted alkylene, alkylidene, substituted alkylidene, arylene, or substituted arylene.

The present invention further includes a compound whose structure comprises:

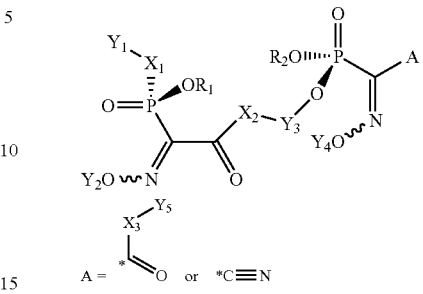

wherein: $X_1$, $X_2$ and $X_3$ are independently selected from the group consisting of: O, $NR_3$, and S; $R_1$, $R_2$, $Y_1$, $Y_2$, $Y_3$, $Y_4$, and $Y_5$, are independently selected from the group consisting of hydrogen, alkyl, aryl, substituted alkyl, and substituted aryl; one of $Y_1$, $Y_2$, and $Y_3$ is selected from the group consisting of: alkylene, oxy-alkylene, amino-alkylene, thio-alkylene, $—(CH_2)_nC(=O)NH—$, $—(CH_2)_nC(=O)O—$, arylene, substituted arylene, heteroarylene, and substituted heteroarylene; at least one of $R_1$ and $Y_1$ is not hydrogen; and at least one of $R_1$, $R_2$, $Y_1$, $Y_2$, $Y_4$, and $Y_5$ is hydrogen; and at least one of $R_1$ and $Y_1$ is not hydrogen.

Figure 6:
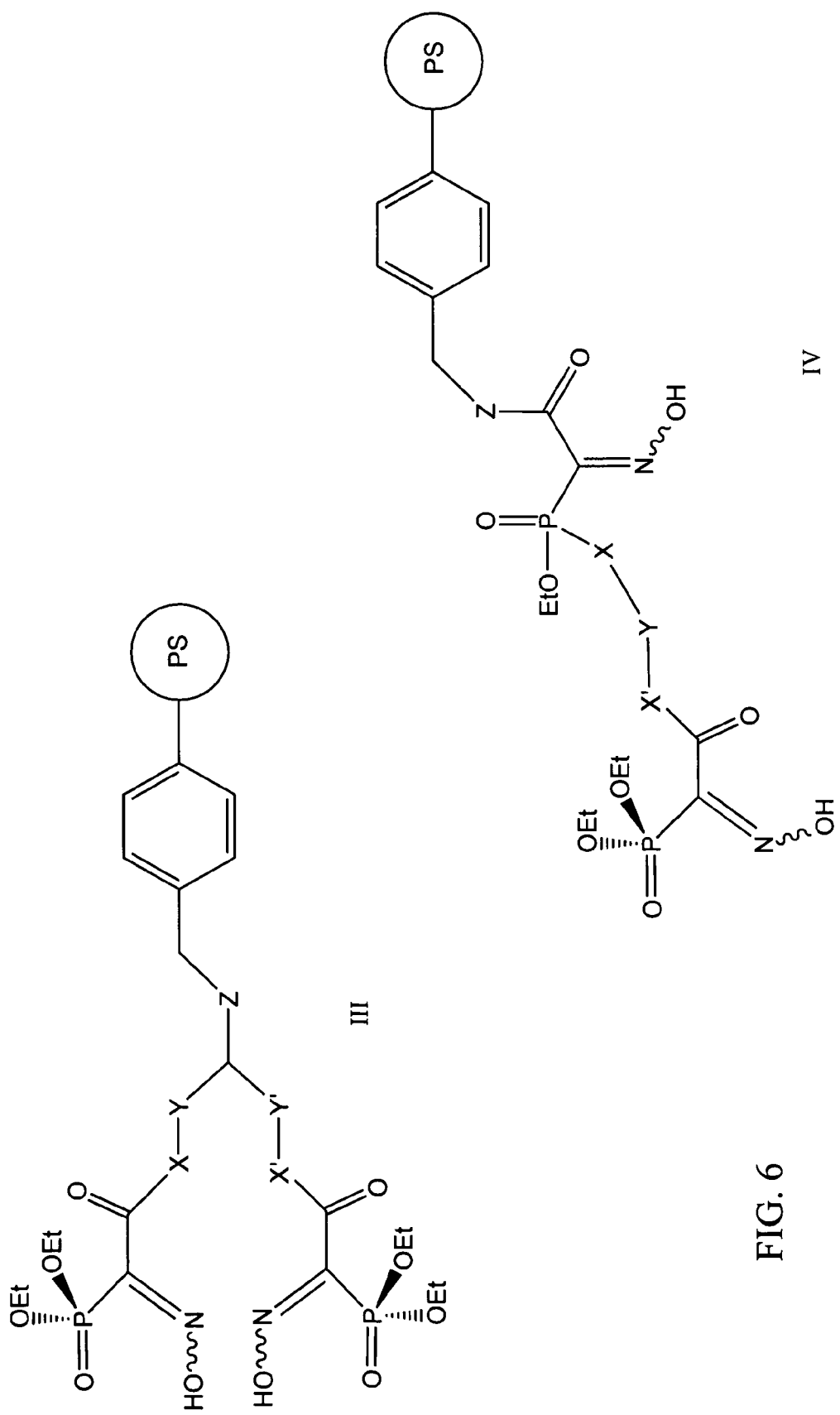
FIG. 6 depicts embodiments of "branched" (III) and "daisychained" (IV) multi-Troika acids (that respectively bind metal ions in parallel (III), and antiparallel (IV) modes) attached to a resin.

In another embodiment of the present invention, multiple Troika acid molecules can share a common attachment point to a polymer support. According to X-ray crystallographic studies of the structure of a model metal ligand complex, Troika acid ligation may be enhanced by providing for multidentate chelation, in which more than one Troika acid is anchored to the resin via a common linking moiety and the metal ion is sandwiched between the two Troika acid molecules, see for example structures III, IV in FIG. 6. In FIG. 6, X, X' are independently heteroatom groups such as O, S, and N(H). Y and Y' are independently spacer groups such as alkylene, alkylidene, or others selected from those described elsewhere herein. Z is also a heteroatom group such as O, S, and N(H).

Figure 7:
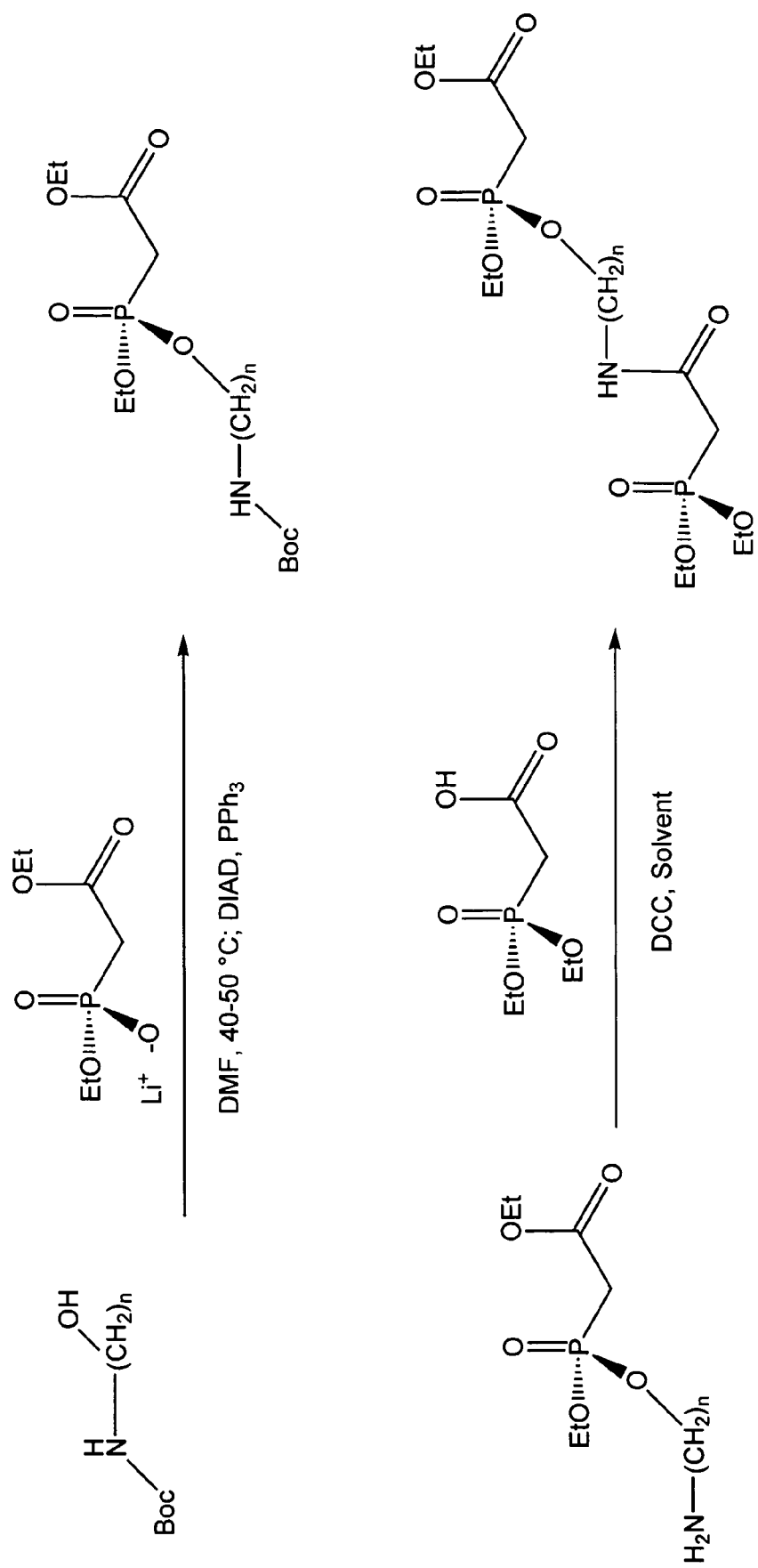
FIG. 7 depicts a preferred reaction scheme to synthesize an exemplary category of multi-Troika acid precursor.

An exemplary synthetic scheme for a multi-Troika acid with more than one Troika acid moiety in a single arm, or else with a branched, or dendrimeric, architecture is disclosed in FIG. 7. In preferred embodiments, each polymer functionalization site is modified with a double ligand containing two conjoined Troika acid moieties separated by a spacer of varying length (see e.g., final product IV, FIG. 6) to facilitate heavy metal chelation by cooperative binding. (Oxime groups are omitted from the compounds in FIG. 7 and can be introduced at later stages of their synthesis using, for example, the techniques of FIG. 3.)

Coupling of a multiple-Troika ligand to a resin employs similar conditions for micro- and macroporous resins as are employed for single Troika ligands respectively.

Applications

The resins of the present invention may be applied to removal of heavy metal ions from water found in a variety of sources such as fossil fuel power plants, nuclear power plants, surface water, industrial waste water, and mining waste water. The present invention may also find applications in groundwater clean-up. In general, one of ordinary skill in the art would be able to deploy the resins of the present invention using techniques known in the field and industry to which the invention is to be applied.

Preferably, the present invention comprises stable Troika acid derivatives that are capable of undergoing repeated regeneration cycles as the metal-removing component of a novel treatment bed material for industrial discharge such as non-nuclear power plant wastewater. The present invention further comprises novel one-time-use heavy metal-removing resins for sequestration of such wastes as radioactive metals from nuclear power plant effluents. The latter embodiment functions in such a way that the recovered metals can be conveniently separated from bulk resin matrix by condition-specific decomposition of the chelating component, (to give phosphate and other small molecules), thereby eliminating all chelating capability. This is particularly important for the long-term disposal of materials contaminated with radioactive components or other heavy metals because it is critical that these materials decompose before disposal and leave no possibility of continued chelating action, but have minimal additional waste generation.

The present invention thus includes a method of removing metal cations from an aqueous medium, comprising: passing the aqueous medium over a macroporous resin, attached to which is a ligand of structure:

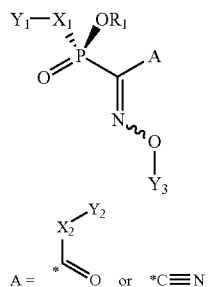

wherein: a starred atom denotes a point of attachment; N~O denotes a bond that represents the Z or E isomeric form; $X_1$ and $X_2$ are independently selected from the group consisting of: O, $NR_4$, and S; $Y_1$, $Y_2$, and $Y_3$, $R_1$, and $R_4$ are independently selected from the group consisting of: hydrogen, alkyl, aryl, substituted alkyl, substituted aryl, and any other suitable spacer group described herein; one of $Y_1$, $Y_2$, and $Y_3$ is absent so that respective group $X_1$, $X_2$, or $X_3$ to which it is bonded is attached directly to the resin, or one of $Y_1$, $Y_2$, and $Y_3$ attaches the ligand to the resin and is selected from the group consisting of: alkylene, oxy-alkylene, amino-alkylene, thio-alkylene, —$(CH_2)_nC(=O)NH$—, —$(CH_2)_nC(=O)O$—, arylene, substituted arylene, heteroarylene, substituted heteroarylene, and any other suitable spacer group described herein; at least one of $R_1$, $Y_1$, $Y_2$, $R_4$, and $Y_3$ is hydrogen; and at least one of $R_1$ and $Y_1$ is not hydrogen.

EXAMPLES

Example 1

Methods and Apparatus

Reagents used in conjunction with the examples presented herein are typically AR grade, as may be ordinarily obtained from commercial vendors. NMR spectra were typically obtained on Bruker 360 or 500 MHz instruments and were referenced to tetramethylsilane ($^1$H, $^{13}$C) or external phosphoric acid ($^{31}$P). Melting points were measured with a Thomas Hoover apparatus. Molecular weights of ligands were determined by high-resolution FAB mass spectrometry. Elemental analysis was performed by Galbraith Laboratories, Inc. Metal ions were tested as chloride or nitrate salts. X-Ray crystallographic analysis was performed using the facilities of the University of Southern California chemistry department.

Synthesis of C-alkyl esters and amides of (hydroxyimino) phosphonoacetic acid was carried out using direct nitrosation of the corresponding P,P-diethyl or P,P-dimethyl phosphonoacetate derivative, with nitrosyl chloride or alkylnitrites (see, e.g., Kashemirov, B. A.; Ju, J.-Y.; Bau, R.; McKenna, C. E., *J. Am. Chem. Soc.*, 117, 7285-7286, (1995); Kashemirov, B. A.; Fujimoto, M.; McKenna, C. E., "(E)-(Hydroxyimino) (hydroxymethoxyphosphinyl) acetic acid: Synthesis and pH-Dependent Fragmentation", *Tetrahedron Letters*, 52, 9437-9440, (1995); and Khokhlov, P. S.; Kashemirov, B. A.; Strepikheev, Y. A., "Nitrosation of Phosphono- and Phosphinoacetic Acid Esters", *J. Gen. Chem. USSR* (Engl.), 52, 2468-2469, (1982)) followed by regioselective dealkylation at phosphorus with bromotrimethylsilane (see, e.g., McKenna, C. E.; Higa, M. T.; Cheung, N. H.; McKenna, M.-C., "Facile Dealkylation of Dialkylphosphonates by Bromotrimethylsilane", *Tetrahedron Letters*, 155-158, (1977); and McKenna, C. E.; Schmidhauser, J., "Functional Selectivity in Phosphonate Ester Dealkylation with Bromotrimethylsilane", *J. Chem. Soc., Chem. Comm.*, 739, (1979)).

Model ligand compounds were purified by chromatography (preparative TLC). Crystallization (see, e.g., Kashemirov, B. A.; Ju, J.-Y.; Bau, R.; McKenna, C. E., *J. Am. Chem. Soc.*, 117, 7285-7286, (1995)). Metal precipitation (see, e.g., Gibson, D.; Karaman, R., *Inorg. Chem.*, 28, 1928-1932, (1989)) was used for separation of E and Z oxime isomers. Assignment of isomers was made on the basis of NMR data, using the known correlation between the α-oxime phosphonate isomer structure and the $^{13}$C NMR $^1J_{PC}$ coupling constant (see, e.g., McKenna, C. E.; Kashemirov, B. A.; Ju, J.-Y., "E/Z Stereoisomer Assignment by $^{13}$C NMR in Trifunctional Phosphonate α-Oximes and α-Arylhydrazones", *J. Chem. Soc. Chem. Comm.*, 1212, (1994)). As the resin bead polymer support, standard commercially available PS-DVB copolymer resins functionalized with nucleophilic $CH_2Cl$ or $CH_2NH_2$ groups were used.

Free metal concentrations were measured using flame atomic absorption spectrometry, with metal-specific lamps.

Example 2

A Comparison of E vs. Z Troika Acid Isomers

Figure 9:
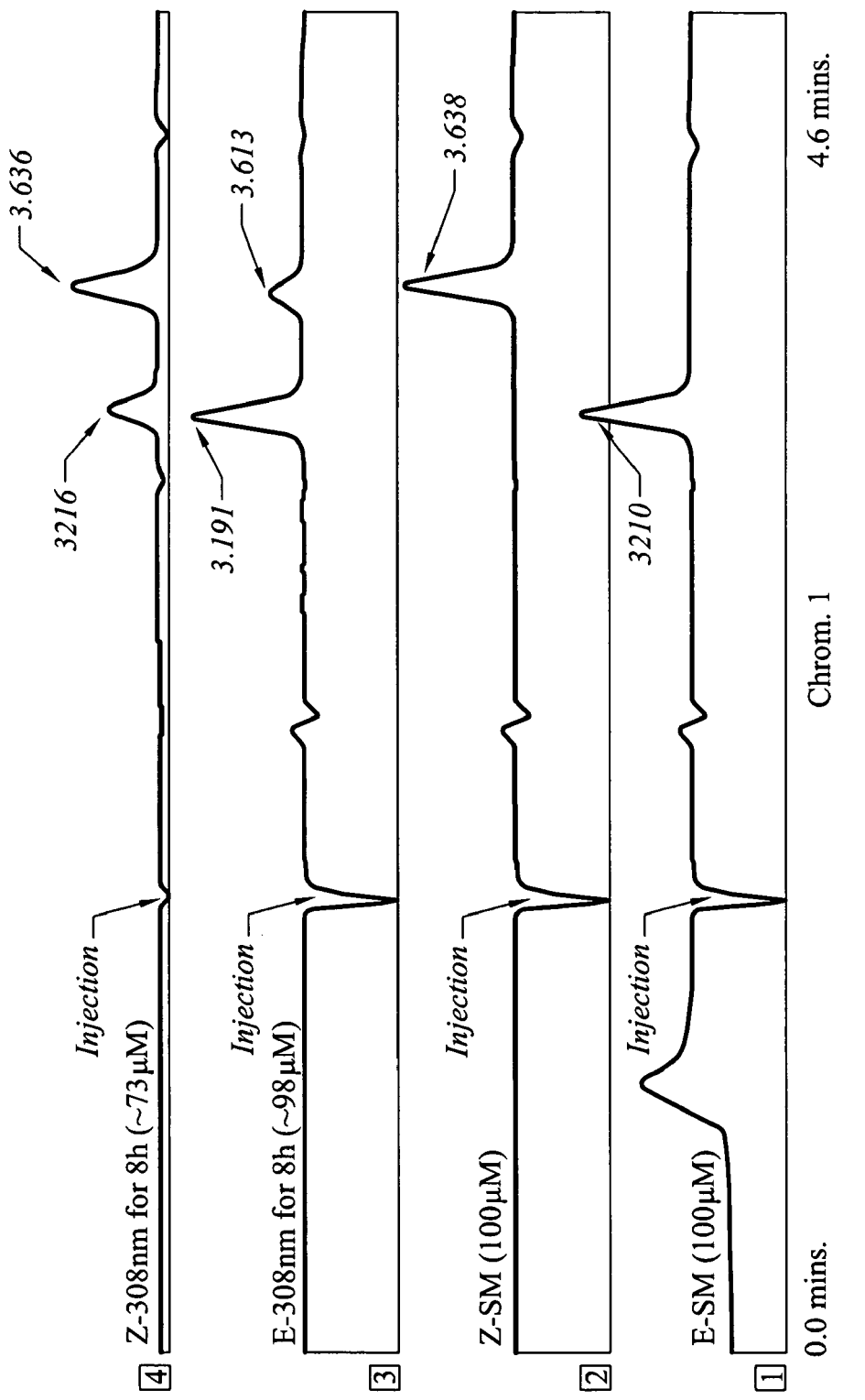
FIG. 9 shows an HPLC trace of various samples containing Troika acid C-methyl ester E and Z isomers.

The structures of the two types of prototypical Troika acid isomers (E/Z) has been defined unequivocally by X-ray crystallography. However, the requirement of a suitable single crystal sample means that X-ray methods are not useful for solution or batch analysis of the many Troika acid derivatives that can be synthesized. An NMR method based on the magnitude of the easily measured $^{13}$C α-C-P spin-spin coupling constant of Troika acid derivatives has found application to distinguish the isomers quickly and reliably (see, e.g., McKenna, C. E.; Kashemirov, B. A.; Ju, J.-Y., "E/Z Stereoisomer Assignment by $^{13}$C NMR in Trifunctional Phosphonate α-Oximes and α-Arylhydrazones", *J. Chem. Soc. Chem. Comm.*, 1212, (1994)). The E and Z isomers of simple Troika acid ester derivatives are also readily distinguished by their UV spectra (see, e.g., Kashemirov, et al., *J. Am. Chem. Soc.*, 117, 7285-7286, (1995)). The separation of a C-nitrobenzyl E/Z Troika acid ester mixture by HPLC, using UV detection has also been demonstrated (see FIG. 9). In FIG. 9, elution times are indicated in minutes and UV detection is at 205 nm. The labeled traces in FIG. 9 are as follows: 1) E isomer 100 μM. 2) Z isomer 100 μM. 3) E/Z mixture created by 308 nm UV irradiation of E isomer (98 μM), 8 h. 4) E/Z mixture created by 308 nm UV irradiation of Z isomer (73 μM), 8 h.

Example 3

Physical Properties of Troika Acid Derivatives

The Troika acids described herein are stable compounds with no known toxicity. Their salts (for $P(=O)(-O)O^-$ or $C(=O)O^-$ derivatives) with organic cations such as dicyclohexyl ammonium ($DCHA^+$), are crystalline substances with well-defined melting points.

Quantum mechanical calculations of the molecular structures of the C-esters (using both the semi-empirical level of theory, and the Hartree-Fock (self-consistent field) method with a 3-21G* basis set and geometry optimizations, using, for example, a computer program such as GAUSSIAN, obtainable from Gaussian, Inc., Wallingford, Conn., or SPARTAN, obtainable from Wavefunction, Inc., Irvine, Calif.) give structural parameters consistent with the bond angles at the central carbon atom obtained from the X-ray structures of the Troika acids.

Example 4

Synthesis of Model Troika Acids

Although the present invention concerns Troika acids bound to solid supports and their applications, evaluation of metal binding affinities and other relevant chemical properties of Troika acids can be carried out on free (model) ligand molecules, studied in the liquid (aqueous) phase. Such model ligands comprise: Troika acid C-esters; Troika oxime NO-ethers; and Troika P-esters. Structures 4, 5, and 6 respectively are examples of such model Troika acid derivatives.

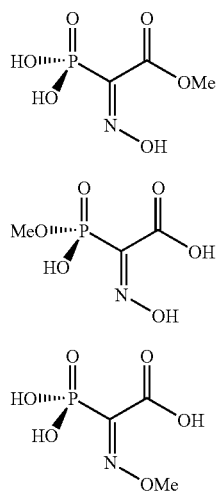

The preparation of simple C-methyl esters of both E and Z Troika acids, such as structure 4, has been described elsewhere, along with their key physical and chemical properties (Kashemirov, B. A.; Ju, J.-Y.; Bau, R.; McKenna, C. E., *J. Am. Chem. Soc.*, 117, 7285-7286, (1995)).

The synthesis and characterization of the E and Z isomers of simple P-methyl monoester Troika acids, such as structure 5, have also been described (see Kashemirov, B. A.; Fujimoto, M.; McKenna, C. E., "(E)-(Hydroxyimino)(hydroxymethoxyphosphinyl) acetic acid: Synthesis and pH-Dependent Fragmentation", *Tetrahedron Letters*, 36(52), 9437-9440, (1995)). The structure of the compounds (as a salt with dicyclohexylamine) was verified by $^1H$, $^{31}P$ and $^{13}C$ nuclear magnetic resonance (NMR) spectrometry and by elemental analysis. Like the corresponding C-ester, this P-monoester compound (which retains one P-OH and therefore carries negative charges on both the phosphonate and carboxylate moieties) proved to be stable in neutral aqueous solutions at ambient temperatures.

A convenient route to a very similar α-phosphono oxime ether, the N-methyl ether of a tetraalkyl α-(hydroxyimino) methylenebisphosphonate, such as structure 6, has been described (see McKenna, C. E.; Kashemirov, B. A., "Preparation and Use of α-(Hydroxyimino)phosphonoacetic Acids", U.S. Pat. No. 5,948,931).

A number of other model compounds based on the Troika acid scaffold have been synthesized, see structures 7-14. The model ligands were characterized by $^1H$, $^{13}C$ and $^{31}P$ NMR spectrometry. Methods of synthesis of such structures and similar structures can be found in Carrick, J., Ph.D. Thesis, "Novel Troika Acid derivatives: Photochemistry and Metal Chelation", University of Southern California, 2000, incorporated herein by reference in its entirety.

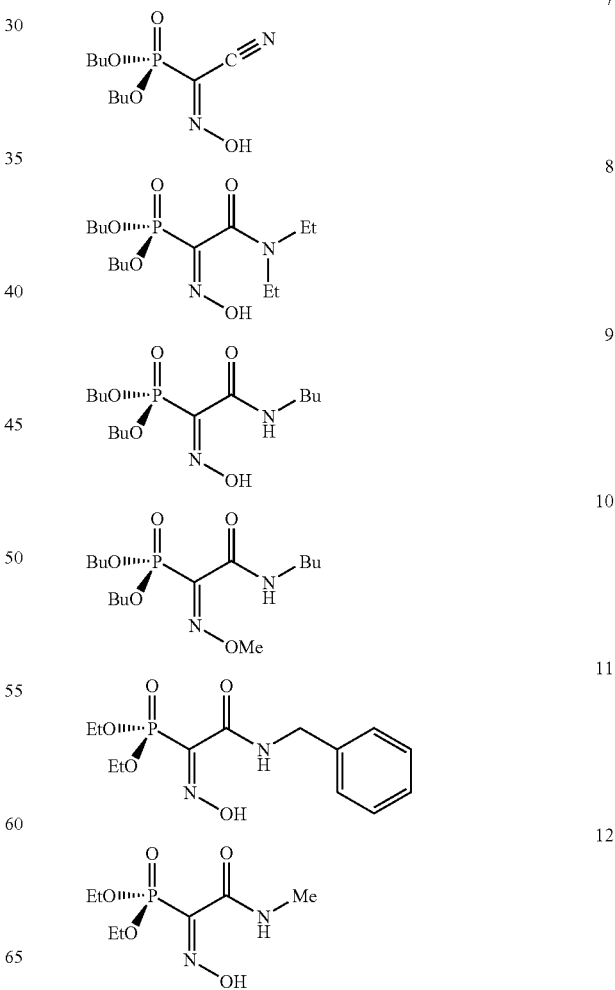

-continued

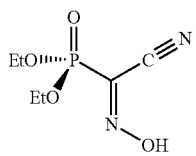

13

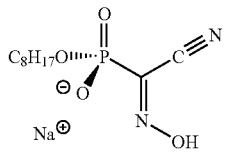

14

These model ligands were tested in organic/aqueous liquid/liquid $Cu^{2+}$ and $Ni^{2+}$ extraction systems, to demonstrate their respective efficacies.

All of these molecules except for 14 contain an electrically neutral (no charge) phosphonate moiety. Structure 14 is the mono P-anionic analog of structure 7 (notice that both molecules contain an identical number of C atoms). Structure 14 was designed to model an alternative linkage strategy that uses a long alkyl spacer between the P group and the resin.

Structures 7-14 permit comparison of the following structural effects on metal binding: a non-amido (structure 7) vs. a dialkylamido group (structure 8); a dialkylamido —$NR_2$ (structure 8) vs. a monoalkylamido —NHR (structure 9) group (the total number of carbon atoms in the groups attached to the amide nitrogen atom in structures 8 and 9 is identical); an —OH (structure 9) vs. an OR (structure 10) oxime =N—OX group; and a resin-like aminomethylstyrene (structure 11) vs. a bulky alkyl, and non-bulky alkyl amido N substituents (structures 9 and 12, respectively), and the less bulky amido variant (structure 13), which is a less bulky P,P-diethyl non-amido analog of 7.

Preferred compounds are those with an amide-type [—C(O)$NR_2$] group on the C-side of the Troika acid (such as structures 8-12). Such compounds model attachment of the Troika acid to a resin such as AMPS via an amide bond. In other embodiments of the present invention, a PO ester link using the P-side of the Troika acid is used.

Example 5

Optimizing Structures of Troika Acids

Metal complexation parameters of Troika acids were determined using established methods for phosphonocarboxylic acids (see, e.g., Farmer, M. F.; Heubel, P.-H. C.; Popov, A. I., "Complexation Properties of Phosphonocarboxylic Acids in Aqueous Solutions", *J. Sol. Chem.*, 10, 523-532, (1981); and Stunzi, H.; Perrin, D. D., *J. Inorg. Biochem.*, 10, 309-318, (1979)).

Troika acid diesters themselves are colorless but have UV absorption. The heavy metal chelates may be isolated as deeply colored powders or crystalline compounds. Complexation of a heavy metal can therefore be detected by the appearance of a color, characteristic of a particular ligand and the complexed metal itself.

UV-visible spectrophotometric or potentiometric data were refined and fit to binding constant parameters using the BEST program (Motekaitis, R. J.; Martell, A. E., "BEST—A new Program for Rigorous Calculation of Equilibrium Parameters of Complex Multicomponent Systems", *Can. J. Chem.*, 60, 2403-2409, (1982)).

Table 2 presents UV-Visible spectra data of some Troika acid heavy metal chelates. The initial spectra, corresponding to the complexes with compounds 7 and 11 have similar strong absorbance peaks in the UV region near 250 nm. Addition of $Cu^{2+}$ or $Ni^{2+}$ leads to formation of chelates which exhibit tails or actual shoulders above 400 nm, in the visible region of the spectrum.

TABLE 2

UV spectra shifts of some model ligands produced by $Cu^{2+}$ or $Ni^{2+}$ complexation.

| | Cu | | | Ni | | |
|---|---|---|---|---|---|---|
| Structure | Model $\lambda_{max}$ (nm) | Chelate $\lambda_{max}$ (nm) | $\Delta\lambda_{max}$ (nm) | Model $\lambda_{max}$ (nm) | Chelate $\lambda_{max}$ (nm) | $\Delta\lambda_{max}$ (nm) |
| 7 | 241.2 | 259.2 | 18.0 | 241.2 | 278.8 | 37.6 |
| 11 | 242.8 | 259.8 | 17.0 | 242.8 | 253.2 | 10.4 |

The model compounds, being neutral esters, dissolve in organic solvents such as chloroform. Thus their ability to remove metal ions from water can be tested using simple extraction procedures familiar to one of ordinary skill in the art. Table 3a displays distribution coefficients measurements. In general, the data in Table 3a show that the non-amido model ligand 7 effectively removes $Cu^{2+}$ from aqueous solution, as does the monoalkylamido model ligand 9. However, the dialkyl amido analog 8 has little chelating power under the same conditions, showing that an NH group is important for chelation. Moreover, when the oxime =N—OH group is capped off with an alkyl group, as in structure 10, almost no chelation is observed. This demonstrates that a free OH group is also important for chelation. Chelation is seen to result in a lowering of the pH, suggesting that the OH group is ionized to —$O^-$. Essentially, the incoming $Cu^{2+}$ ion must displace one or more $H^+$ ions from OH groups in the Troika acids. Finally, the data show that increasing the initial pH of the aqueous solution containing the $Cu^{2+}$ ions increases the amount of chelation, suggesting that lowering the pH could provide a means to release the chelated metal ions and regenerate the ligand.

TABLE 3a

Effect of Hydroxyiminophosphonate structure on liquid-liquid $Cu^{2+}$ extraction. Initial pH is prior to extraction, and final pH is post-extraction.

| | Distribution Coefficient Measurement | | | | | |
|---|---|---|---|---|---|---|
| Model Compound | Initial pH = 5.02 (200 mM Acetate) | Final pH | D | Initial pH: 6.37-6.70 (200 mM Acetate) | Final pH | D |
| 7 | 5.02 | 4.77 | 1.58 | 6.37 | 5.36 | 7.12 |
| 8 | 5.02 | 5.02 | 0 | 6.37 | 6.00 | 0.41 |
| 9 | 5.02 | 4.71 | 4.56 | 6.37 | 5.44 | 7.32 |
| 10 | | | | 6.70 | 6.62 | 0.04 |
| 11 | | | | 6.70 | 5.35 | 4.43 |

D is defined as the Distribution Coefficient: D = [$Cu^{2+}$ in $CHCl_3$]/[$Cu^{2+}$ in aq]

The profound effect of model Troika acid structure on chelating ability may be illustrated by comparison of the colors of various solutions. In a control tube, the Cu (evidenced by a light blue color) remains in the upper, aqueous, layer whereas the lower chloroform layer is colorless. Addition to the lower layer of the =N—OR "capped" oxime compound 10, or compound 8 which has an =N—OH group but no —C(O)NH— group, fails to noticeably remove $Cu^{2+}$ from the aqueous phase. The Troika acid nitrile compound 7 effectively and dramatically removes the $Cu^{2+}$ from the water, giving a green-colored chelate in the lower organic phase. Model ligand 9, which contains both =N—OH and —C(O)NH— groups, also effectively removes the $Cu^{2+}$, giving in this case a deep brown complex in the organic phase.

Table 3b shows that model compounds 7 and 11 are far better chelators of $Co^{2+}$ than $Ni^{2+}$.

TABLE 3b

Example Cobalt and nickel extraction data.

| | Distribution Coefficient Measurement | | | | | |
|---|---|---|---|---|---|---|
| | $CoCl_2$ | | | $NiCl_2$ | | |
| Model Compound | Initial pH = 6.00 (25 mM $CoCl_2$) | Final pH | $D_{Co}$ | Initial pH: 6.36 (25 mM $NiCl_2$) | Final pH | $D_{Ni}$ |
| 7 | 6.00 | 5.90 | 7.33 | 6.36 | 5.42 | 0.27 |
| 11 | 6.00 | 5.90 | 6.35 | 6.36 | 5.31 | 0.53 |

$D_{Co} = [Co^{2+} \text{ in } CHCl_3]/[Co^{2+} \text{ in aq}]$;
$D_{Ni} = [Ni^{2+} \text{ in } CHCl_3]/[Ni^{2+} \text{ in aq}]$ Using the rate of release of the easily detected p-nitrophenolate ion as a UV-visible spectrophotometric marker (see, e.g., Kashemirov, B. A., et al., *Phosphorous, Sulfur, Silicon and Related Elements*, 981, (1999)), it was found that at equivalent concentrations (at pH >6), added $Ni^{2+}$ accelerated hydrolysis of p-nitrophenyl-E-hydroxyiminophosphonoacetate by nearly three orders of magnitude more than added $Mg^{2+}$. An analog in which the C=N—OH oxime function was replaced by a simple methylene ($CH_2$) had marginal response to added $Ni^{2+}$ ion, showing the key role played by the oxime group in conferring both high $Ni^{2+}$ affinity and dication selectivity.

Example 6

X-Ray Structure of a Troika acid-Ni Complex

Figure 10:
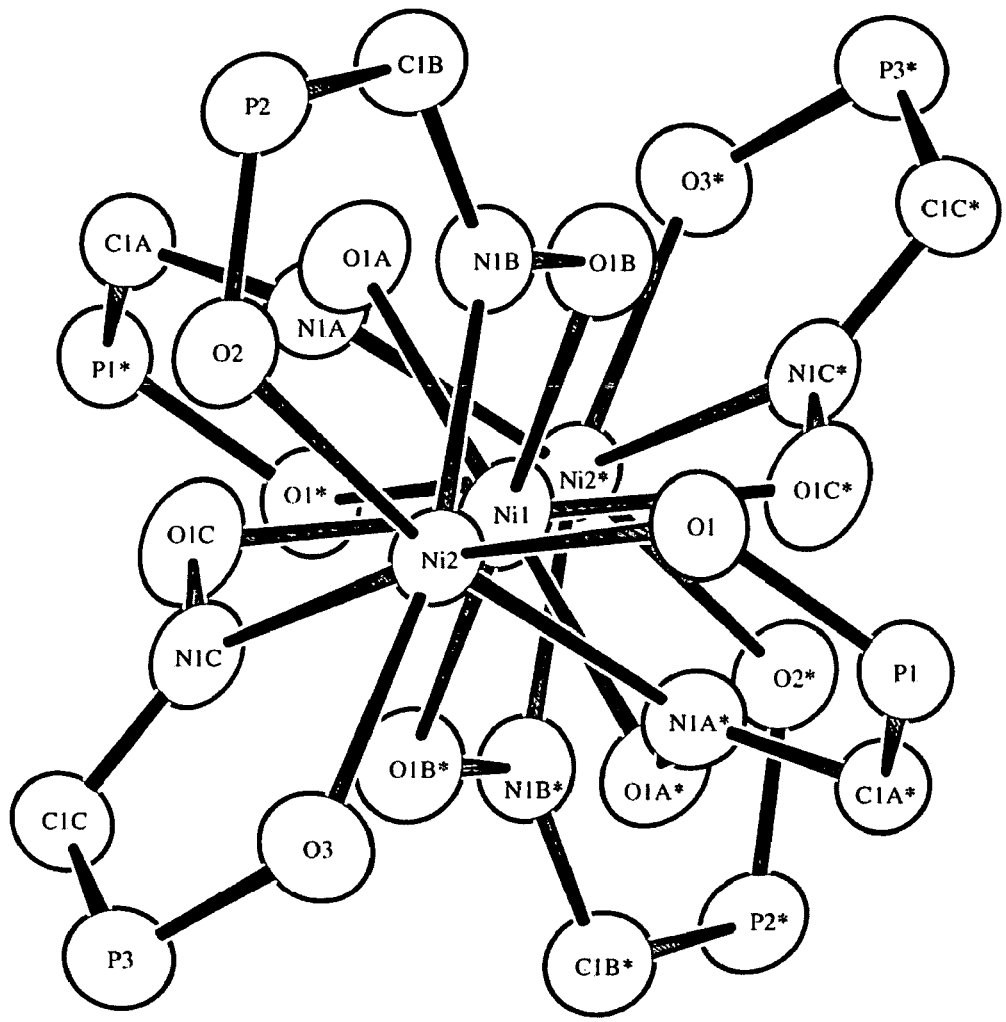
FIG. 10 shows an X-ray structure of the core of a 'Troitsa' chelate of $Ni^{2+}$ with the ligand P,P-diethoxy N-benzyl Troika acid carboxamide (only those atoms directly involved in chelation are shown)

A single crystal of $Ni^{2+}$ complexed with compound 11 was formed using methods described herein, and analyzed by X-ray crystallography. The structure of the complex, which consists of three nickel ions coordinated by six Troika acid molecules, is shown in FIG. 10. Only those atoms directly involved in chelation are show in FIG. 10. The view is along the Ni—Ni—Ni axis. Each starred atom (*) has a symmetrically equivalent unstarred atom. Single crystal data collection and analysis was carried out at USC. This structure has been called a "Troitsa", meaning 'trinity', complex because it has three nickel atoms. It does not require any external solvent ligand (such as $H_2O$ or $OH^-$) to stabilize it—the tripodal Troika acid molecule can, on its own, wholly coordinate the nickel ions.

The three nickel cations form vertices of a broad-based isoceles triangle in which the symmetrically unique nickel atom is referred to as "inner" whereas the other two are referred to as "outer". The oxime N, O and phosphonate O atoms derived from the three pairs of ligand molecules coordinate three Ni atoms octahedrally, in two different modes. The inner nickel ion is coordinated by six oxime O atoms. The positive charges of the 6 protons displaced from the oxime groups are balanced by the total of 6 positive charges from the three $Ni^{2+}$ ions. Each outer nickel ion is coordinated by three oxime N atoms and three phosphonate O atoms. The carboxyamide benzyl ("Bz") groups pendant around the equator of the complex simulate C-amido attachment to a resin styrene-benzene polymer backbone The three $Ni^{2+}$ ions thus form a metal core, surrounded by hydrophobic groups on the periphery, rather like a nickel wire surrounded by its plastic insulation (except that there is no evidence for metal-metal electron delocalization in the Troitsa complex).

This structure shows that, in solution, nickel ions are probably coordinated by multiple Troika ligands, and also that, in solution, the oxime group is likely to be ionized.

Example 7

Ligand Functionalization Studies with Microporous Resins

Functionalization of a ligand on a microporous or macroporous resin are examples of solid support chemistry which have different characteristics from either homogeneous reactions in solution, or heterogeneous reactions taking place at the interface of a solid surface. Thus, reactions with microporous resins are intermediate between homogeneous and heterogeneous reactions due to the effective swelling of the resin and the formation of gels in different organic solvents. When designing a macroporous resin suitable for removing ions from water and devising solid phase synthetic routes to Troika acid-functionalized resins it is instructive to consider a microporous resin. Accordingly, model Troika acid compounds with favorable liquid-liquid extraction properties were selected for incorporation into a solid microporous polystyrene resin for purposes of study.

The base microporous resin selected (denoted RO, and referenced herein as PS-DVB) was polystyrene (PS) cross-linked (1%) with divinylbenzene (DVB), 200-400 mesh, aminomethyl functionalized, 0.6 molar equivalents of amine/g resin. Although not suitable for aqueous solutions, the microporous resin readily swells in organic solvents, to form a gel in which derivatization reactions can be followed step-by-step using standard solution phase nuclear magnetic resonance ($^{31}P$ NMR) spectrometry. In contrast, special NMR techniques (such as solid state NMR) are usually required for macroporous resin analysis, and spectral linewidths are broad, rendering analysis more difficult and less definitive.

Attachment of diethyl phosphonoacetic acid to the aminomethyl function of the PS-DVB resin can be achieved with a coupling agent such as DCC (dicyclohexylcarbodiimide) (see FIG. 3). The Troika acid oxime function can then be introduced into the phosphonate, i.e., after resin immobilization. Conditions employed for, e.g., diethyl ester of phosphonoacetic acid on a microporous amino (PS-DVB) resin are as follows: Chloroform and DCC:resin in a molar equivalent ratio of 1:1 at room temperature, giving rise to a reaction that is practically complete in about 1 hr.

This approach gives rise to two practical difficulties. First, it is preferable to ensure that all of the resin amino groups react; second, it is preferable to be able to observe the phosphonate group after resin attachment, thereby permitting the next step—introduction of the oxime function to create a Troika acid—to be monitored.

Completeness of reaction of the resin amino groups may be monitored using a method of fluorometric detection known to one of ordinary skill in the art (see, e.g., Felix, A.; Jimenez, M., "Rapid Fluorometric Detection for Completeness in Solid Phase Coupling Reactions", *Anal. Chem.*, 52, 377-381, (1973)). The reagent fluorescamine reacts with amino groups to form a fluorescent group (fluorophore). Thus, any unreacted amino groups can be detected by illuminating the material with a UV light. Small amounts of different samples were placed in glass Petri dishes and observed under UV light. The starting aminomethyl resin treated with the fluorescamine reagent, gave a bright green fluorescence, indicating the presence of unreacted amino groups. In contrast, the control—untreated resin—simply reflected the purple-blue UV light. For resin that had been exposed to phosphonoacetate under coupling conditions, some fluorescence is still apparent when compared to the control. However this fluorescence completely disappears in resin that was exposed twice to the phosphonate-coupling reagent cocktail. A notable feature of this method of detection is its great sensitivity: in practice, undetectable fluorescence corresponds to better than 99.5% successful coupling.

The second issue is that the solid, insoluble nature of the derivatized resin, complicates routine NMR analysis of the material. NMR provides useful information about H, C and P atoms in a phosphonate compound, but normally requires a liquid sample. Although solid-state NMR may be used, a more preferred method is gel phase NMR (see, e.g., Johnson, C. R.; Zhang, B., "Solid-phase synthesis of alkenes using the Horner-Wadsworth-Emmons reaction and monitoring by gel-phase $^{31}$P NMR", *Tetrahedron Letters*, 36, 9253-9256, (1995)). This technique takes advantage of the fact that some resins swell in certain organic solvents to form a transparent gel. Microporous resins used with the present invention readily gel in deuterochloroform.

Figure 11:
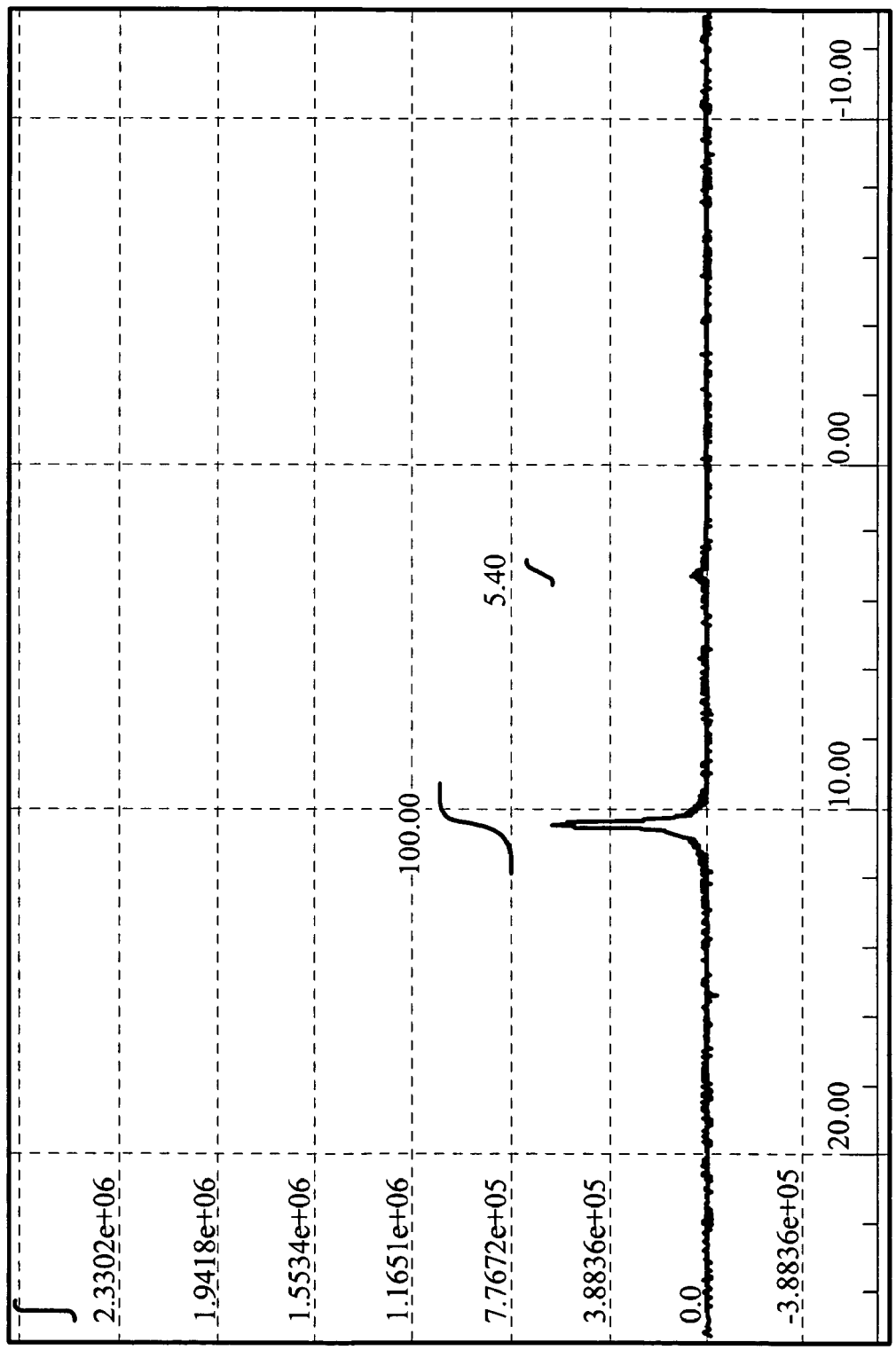
FIG. 11 is a $^{31}P$ NMR of a Troika acid immobilized on a microporous resin, gel phase sample.

A $^{31}$P NMR spectrum of the derivatized resin gel clearly shows that only one major type of phosphonate group is present. Moreover, the peak (which is only slightly broadened relative to typical peaks in solution NMR spectra) clearly identified this group as a diethyl phosphonoamide by its chemical shift value of δ=24 ppm. Thus the progress of the next step, conversion of the phosphonoacetate moiety to Troika acid, could be easily monitored. It was also possible to easily distinguish E from Z isomer forms of the oxime ligand, where both were present (in FIG. 11, the small upfield peak is assigned to the Z isomer). Thus, the final model resin was created in only two synthetic steps from R0, due to its convenient aminomethyl functionalization.

Several other test microporous resins were created using similar techniques by binding PS-DVB with different types of Troika acid-derived ligands, as shown in structures 15-18.

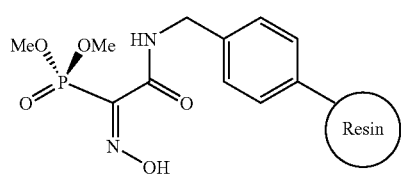

15

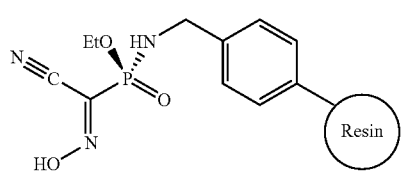

16

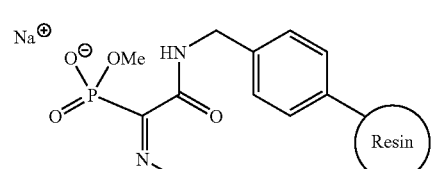

17

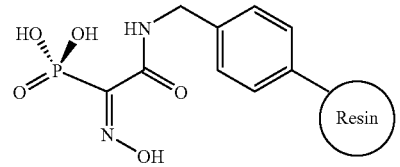

18

The $Cu^{2+}$ binding properties of these Troika acid derivatized resins were compared to underivatized Chelex™, see Table 4. Chelex (capacity: 2.0 meq; 100-200 mesh; sodium form) may be used as a commercial benchmark in evaluating the properties of resins used with the present invention. Chelex, a macroporous resin, is based on the N,N-diacetate ligand and is a weak acid cation exchanger.

The effect of organic-solvent promoted swelling on metal chelation in the microporous resins is apparent from the data in Table 4. All Troika acid derivatized microporous resins abstracted the heavy metal from polar organic solvents, but not from aqueous buffer, whereas Chelex showed the opposite behavior, removing heavy metal ions from aqueous solutions more effectively than from polar organic solvents. Having started with only 0.6 mmol/g of amine functionality (starting resin used in synthesis prior to Troika acid functionalization), three out of four resins showed capacities between 0.43 and 0.47 mmol/g resin. As a control, Chelex 100 (sodium form) was tested under the same conditions, and showed no chelation from the organic solvent, but good chelation in the aqueous solution. Industrial batch analysis for the sample of Chelex 100 indicated a 0.6 mmol/g capacity; the experimental results herein were in good agreement at 0.59 mmol/g.

TABLE 4

$Cu^{2+}$ chelation properties of some microporous Troika acid resins vs. Chelex, expressed as a capacity, in mmol per gram of resin.

| Resin | Dioxane/MeOH (1:1) 24 hr. | Dioxane/MeOH (1:1) 48 hr. | 0.6 M Acetate Buffer, 24 hr | 0.6 M Acetate Buffer, 48 hr |
|---|---|---|---|---|
| Chelex 100 | 0 | 0 | 0.59 | 0.59 |
| 15 | 0.43 | 0.43 | 0 | 0 |
| 16 | 0.29 | 0.29 | 0 | 0 |
| 17 | 0.45 | 0.45 | 0 | 0 |
| 18 | 0.47 | 0.47 | 0 | 0 |

Example 8

Attaching a Troika Acid to a Macroporous Resin

With most resins for use with the present invention, one preferred approach is to attach a preformed Troika acid to the resin, thereby saving one synthetic step. In another approach, a Troika precursor is attached to the resin and is subsequently derivatized to form the Troika. In any of these cases, it may be necessary to first derivatize the resin so that the Troika acid may be attached to it.

Figure 12:
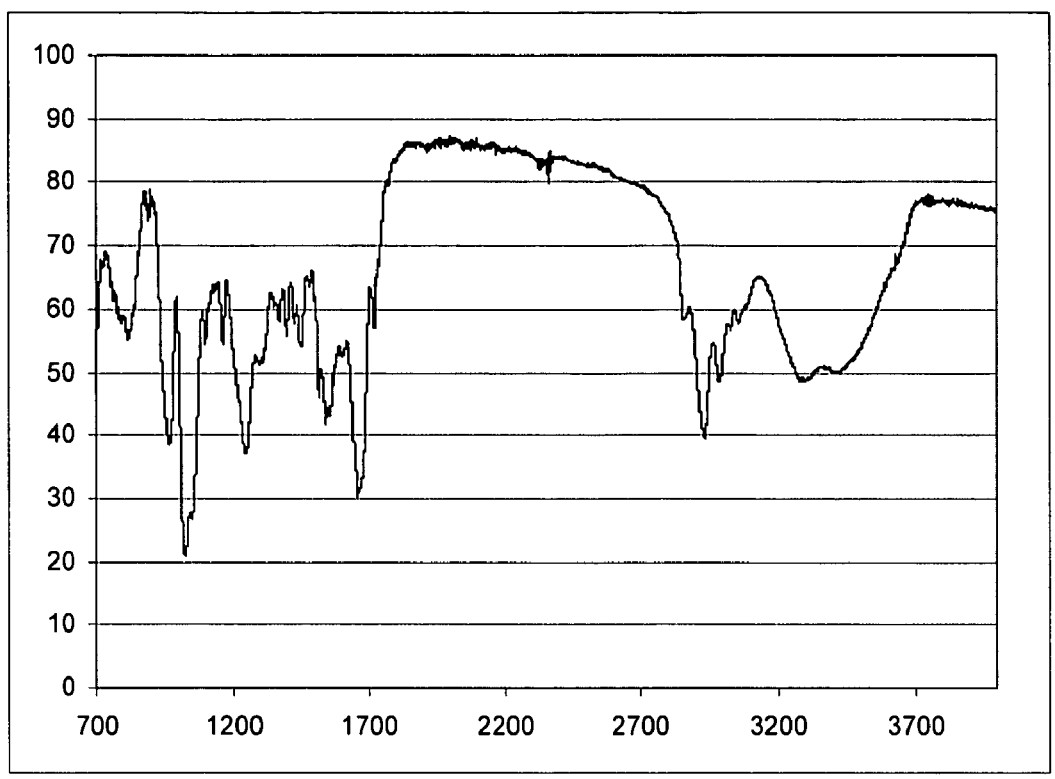
FIG. 12 is an IR spectra of a macroporous amino (PS-DVB) resin after immobilization of the diethyl ester of phosphonoacetic acid on it.

To optimize reaction conditions (such as duration of reaction, concentrations of the various reagents, choice of solvent, and reaction temperature) we used an improved FTIR method for analogous resin compositions that permits measurements on solid materials (see, e.g., Liao, J. C., Beaird, J., McCartney, N., DuPriest, M. T., "An improved FTIR method for polymer resin beads analysis to support combinatorial solid-phase synthesis", *American Laboratory*, 32 (14): 16-20, (2000)). A Spectrum 2000 FTIR (from Perkin Elmer) was used to obtain infrared spectra of the samples employing a DiasqueezePlus diamond compression cell and Microfocus beam condenser (Specac, Inc.). The ZnSe beam condenser had a working range of 550 $cm^{-1}$ to 4000 $cm^{-1}$. The course of the reactions was followed by monitoring the P=O band (at 1200-1300 $cm^{-1}$), the C=O band (at 1500-1700 $cm^{-1}$), and the NH and OH bands (at 3000-3700 $cm^{-1}$). An example of a spectrum of a derivatized resin is shown in FIG. 12.

Direct Attachment of a Troika Acid

In a coupling scheme according to FIG. 4, to immobilize hydroxyimino(diethylphosphono)acetate directly to a PS-DVB a minoresin, trityl protected hydroxyiminophosphonoacetic acid was used. Reaction was carried out in dry DMF in the presence of a 6-fold excess of DCC at 45° C. for 24 hr. It is consistent with this technique that temperatures in the range 40-50° C. can be used, and that reaction times in the range 12-30 hours are effective. Deprotection (after multiple washing of resin with methanol and drying), was conducted with 5% TFA in chloroform for 3 hours at room temperature. Alternative conditions suitable for the purpose include use of solutions of 5-15% TFA in chloroform or dichloromethane for times in the range 2-5 hours, and temperatures in the range 10-35° C.

Attachment of a Troika Precursor Followed by Derivatization

In such a scheme, the first step is to attach a Troika precursor to the resin. For example, the preferred conditions of immobilization of the diethyl ester of phosphonoacetic acid on a macroporous amino (PS-DVB) resin are as follows: DMF, with DCC:resin in a molar ratio of 6:1, at 45° C. for 16 hours. The solvent that is needed for immobilization of diethylphosphonoacetate on a macroporous resin is more polar than that for the corresponding microporous resin (in order to achieve better swelling). A preferred solvent is di-methyl formamide (DMF). Also, a 6-fold excess of coupling agent is deployed along with a higher reaction mixture temperature, and a prolonged reaction time relative to that used for microporous resins.

In order to load more phosphonate onto the resin, this reaction can be repeated up to two additional times with a careful resin wash after each step. We came to this conclusion based on FTIR analysis. We followed the intensities of P=O and C=O groups in IR spectra of resin at 16 hours (first reaction), 32 hours (first repetition), and 48 hours (second repetition). We found a large difference between the intensities of the IR bands corresponding to the resin P=O and C=O groups after 16 and 32 hours, but practically no difference between the intensities at 32 and 48 hours. We concluded that the reaction should preferably be repeated 2-3 times with a total reaction time of 32-48 hours.

Due to the heavy consumption of DCC and the difficulties in washing of dicyclohexyl urea (a byproduct of reaction between water and DCC) from the resin surface, another approach for phosphonate immobilization on a macroporous resin was devised. Such an approach involves reaction with phenyl phosphonoacetate in toluene at room temperature for 9 hours. Other reaction conditions suitable for achieving this step include use of para-nitro phenyl phosphonoacetate, concentrations in the range 0.1-0.3 M, and reaction times in the range 2-9 hours depending upon the reagent employed.

In a second step, immobilization of the oxyimino function may be achieved by reacting an oximating agent, such as NOCl or PrONO, with the macroporous resin. This reaction is preferably carried out in dioxane. For macroporous resins a 9 hour reaction time for this step is preferred, which is to be compared with a 3 hour time for a microporous resin. In general, other acceptable conditions include temperatures in the range 10-25° C., and use of toluene as a solvent. The preferred oximating agent for a macroporous resin is NOCl (nitrosyl chloride). This is to be compared with propionitrite (PrONO) for a microporous resin. Use of NOCl provides better conditions for the nitrosation (oximation) reaction with macroporous resins due to the absence of propyl alcohol (which forms from propionitrite in reaction with HCl). Presence of propyl alcohol worsens amide group protonation (which is necessary for C-nitrosation) and decreases the concentration of the active species, NOCl. (Additionally, when using PrONO, formation of nitrosyl chloride from propionitrite and HCl is reversible due to the presence of propyl alcohol in the reaction mixture).

Example 9

Ligand Functionalization Studies with Macroporous Resins

A preferred base derivatized polystyrene resin (denoted R2, herein) has chloromethyl functionality (—$CH_2Cl$) with a particle size of 250 microns, and a crosslinkage of 6%. A drawback of R2 is the fact that its chloromethyl groups must be converted to aminomethyl groups for subsequent coupling. Accordingly, in a preferred embodiment of the former approach, the chloro group in R2 can be converted to the desired amino functionality using the Gabriel reaction (see, e.g., D. J. Cram and G. S. Hammond, *Organic Chemistry*, p. 214, New York, 1959). The success of this reaction can be confirmed by HCl titration of the amino groups.

With R2, the success of the Gabriel reaction was confirmed by HCl titration of the amino groups. The results indicate that the amination reaction proceeded with virtually 100% completion, giving 5.2 meq/g resin. By comparison, the amino titer of a commercially available microporous resin (denoted R0) was only 0.6 meq/g. R0 is (aminomethyl)polystyrene, available from Sigma Chemical company (product number 08566) with a capacity for the amine of ~0.6 mmol/g of resin. It comprises a crosslinked matrix with 1% DVB and a particle size of 200-400 mesh.

A Troika acid was joined to R2 in 2 steps. Conditions to couple diethyl phosphonoacetic acid to the aminated R2 (step 1) are: DMF, 6 eq. DCC, 45-70° C. Conditions for incorporating an oxime group after immobilization (step 2), resulting in the creation of a macroporous Troika acid resin, denoted MP-1, are as follows: PrONO, HCl gas, dioxane, or NOCl in dioxane.

The metal-binding properties of this resin (MP-1) were investigated by exposing it to an aqueous solution of a heavy metal ion, stripping the bound metal from the resin using acid, and analyzing the recovered metal by flame atomic absorption spectroscopy (using, e.g., a Perkin Elmer 2380 AAS spectrometer, P-E $Cu^{2+}$ lamp, $C_2H_2$-air flame). The presence of the active, immobilized ligand is clearly demonstrated by the heavy metal-binding properties of this resin, and by the greenish color of the bound $Cu^{2+}$ complex which is consistent with a copper oxime complex, and dramatically different from the blue $Cu^{2+}$ complex of Chelex™, or the starting amino resin.

The modified resin is highly selective for $Cu^{2+}$ vs. $Mg^{2+}$ or $Ca^{2+}$. The $Cu^{2+}$ chelating capacity of this resin decreased only 1.3 times from solutions containing $Mg^{2+}$ ions ($10^4$ excess), compared with only 1.5 for Chelex™. Thus, chelation capacity is not changing very much when background ions are present. With solutions containing background $Ca^{2+}$ salts ($10^4$ excess), the corresponding values were 2 and 1.6 respectively.

Another preferred commercially available polystyrene resin (denoted R1) has aminomethyl functionality (obtainable from, e.g., Aldrich, Inc., product ID 564109) with a bead size of 70-90 mesh, with a cross-linkage of 8%. R1 gives an extent of labeling of around 1.5-3.0 mmol per gram (i.e., the resin is labeled with amino group at a proportion of 1.5-3.0 mmol of amino groups per 1 gram of dry resin).

A second more preferred Troika acid resin, MP-2, is based on resin R1. MP-2 offers significant advantages over MP-1: it has a higher density of potential linking sites; it swells more in organic solvents, providing better interior access to reagents, again offering the possibility of higher ligand density (more metal binding capacity/g resin) and more reliable derivatization chemistry; the resin is commercially available in aminomethyl, not chloromethyl, form thereby saving one synthetic step potentially leading to improved yield; it has a higher level of cross-linking (8% vs. 5%); and it is cheaper to obtain on a bulk scale.

Example 10

Relative Binding Stabilities of Sandwich Chelates

Figure 5:
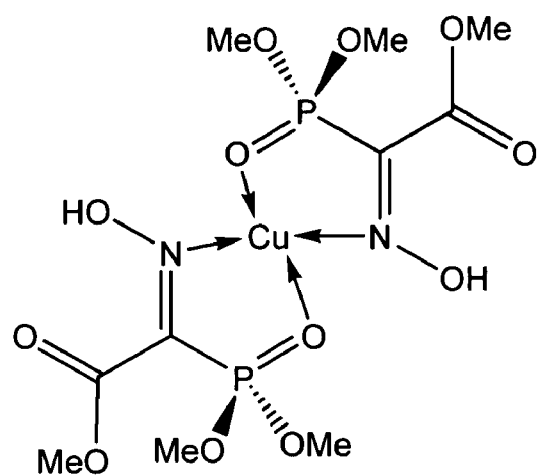
FIG. 5 depicts structures (I, II) of representative $Cu^{2+}$ complexes used to calculate the difference in energy between parallel (II) and antiparallel (I) configurations of a copper complex simultaneously chelated with two Troika acids.
Figure 5:
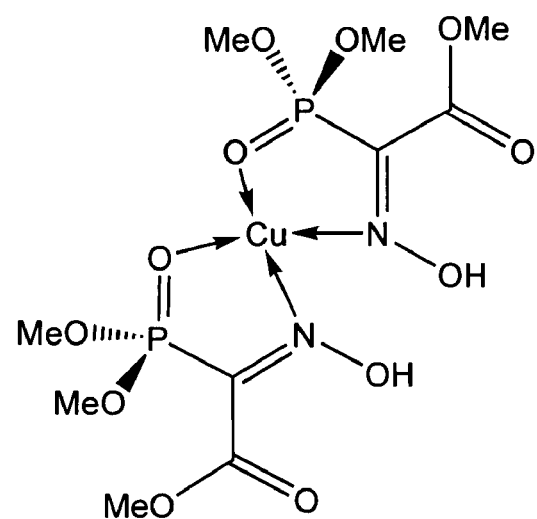

In 'sandwich' chelates, two Troika acid moieties can complex a single metal ion in either of two ways, 'cis' (III) and 'trans' (IV) (equivalent to "parallel" and "antiparallel", respectively, in FIG. 6). When designing ligands, it is important to know whether the two binding modes are significantly different in energy. An ab initio quantum mechanical electronic structure calculation for each ligand complexed with $Cu^{2+}$ (FIG. 5, structures I, II) shows that the energy difference is small (0.2 kcal/mole), meaning that either orientation is likely. Such an appreciation is relevant to Troika acids bound to a resin because it demonstrates that, in certain circumstances, a metal ion may be coordinated by a pair of Troika acid functions.

Example 11

Synthesis of a Multi-Troika Acid Bound to a Resin

Figure 8:
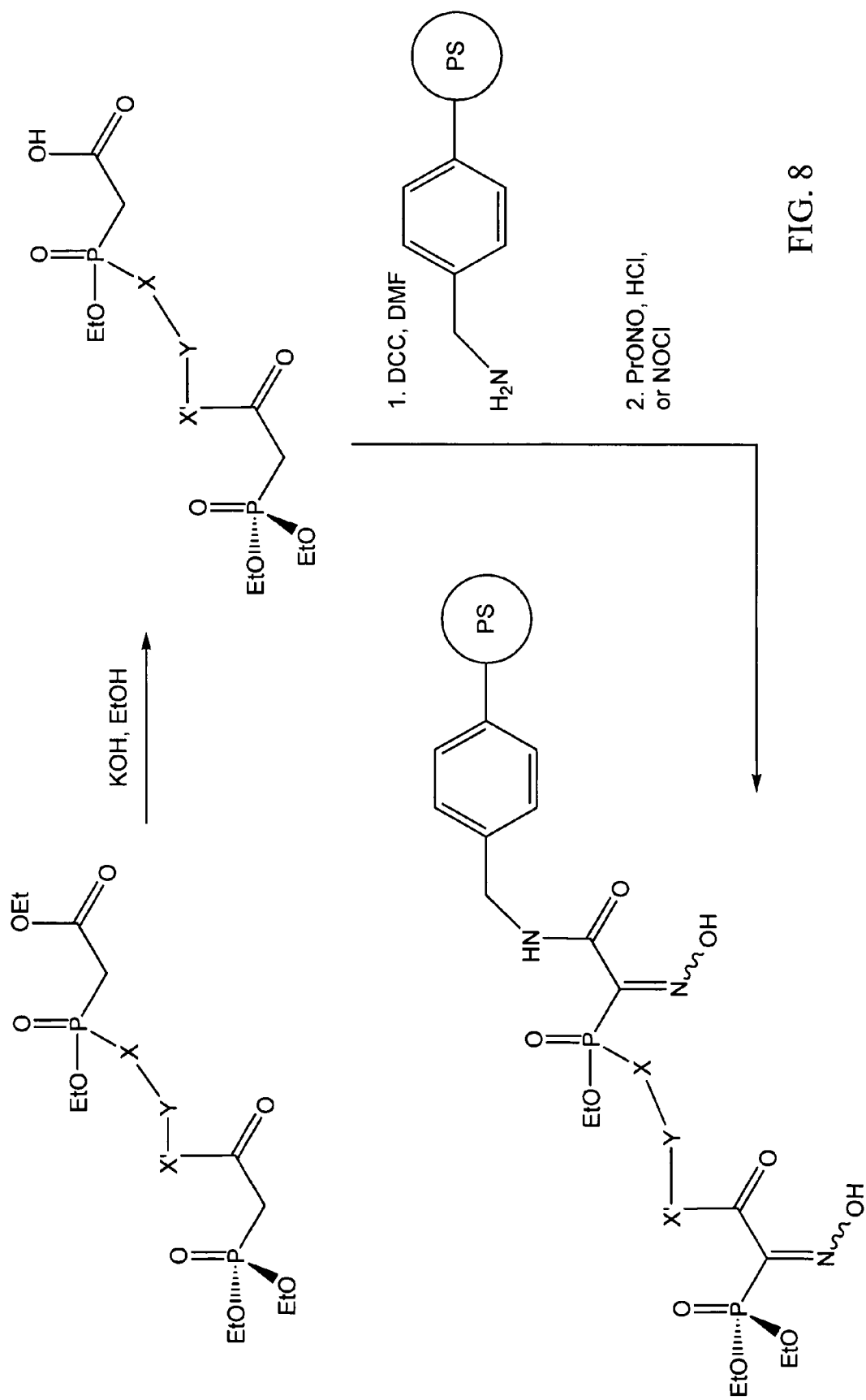
FIG. 8 depicts a method for coupling an exemplary multi-Troika acid precursor to a methyleneamino-functionalized resin such as a microporous resin, or a macroporous polystyrene resin.

To synthesize target IV (see FIGS. 6, 7 and 8) according to a preferred synthetic scheme, triethyl phosphonoacetate is converted to its monolithium salt, followed by Mitsunobu condensation with 5-aminopentanol, in which the amino group is protected by a Boc function such as may be provided by treatment with di-t-butyl dicarbonate. A resin, such as a polystyrene resin, is then treated with N,N'-di-t-Boc-2-hydroxy-1,3-diaminopropane in THF, followed by potassium hydroxide and tetrabutylammonium hydrogensulfate. The blocked linking amino groups are deprotected using methanolic hydrochloric acid, and the resulting hydrochloride salts are neutralized with methanolic ammonia. After de-esterification at the ethyl carboxylate group using potassium hydroxide in 75% of ethanol, the daisy-chained ligand precursor is attached to the amino resin via a carboxamide bond (DCC, DMF; FIG. 8), and nitrosation is carried out, as described hereinabove, to complete the ligand oxime function.

Example 12

Coupling of Multiple Troika Ligands to Microporous and Macroporous Resins

Differences in immobilization of diphosphorus ligand and oxymino function between microporous and macroporous resins are similar to those mentioned in connection with FIG. 2: in general a more polar solvent (DMF versus chloroform) is required for a macroporous resin, as well as a higher reaction temperature (e.g., 40-70° C. versus room temperature). Prolonged reaction time, excess of reagents, and use of more a powerful nitrosating agent (NOCl versus propionitrile) are also preferred in connection with attaching a multiple Troika acid to a macroporous resin.

All references cited herein are expressly incorporated by reference in their entirety for all purposes.

The foregoing description is intended to illustrate various aspects of the present invention. It is not intended that the examples presented herein limit the scope of the present invention. The invention now being fully described, it will be apparent to one of ordinary skill in the art that many changes and modifications can be made thereto without departing from the spirit or scope of the appended claims.

What is claimed:

1. An apparatus comprising a resin attached to a compound comprising

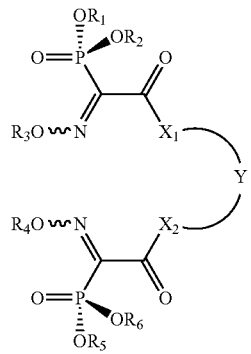

wherein $R_1$, $R_2$, $R_3$, $R_4$, $R_5$, and $R_6$ are selected from the group consisting of hydrogen, alkyl, aryl, substituted alkyl, and substituted aryl; at least one of $R_1$ and $R_2$ is not hydrogen; at least one of $R_5$ and $R_6$ is not hydrogen; $X_1$ and $X_2$ are each independently selected from the group consisting of O, $NR_7$, and S, wherein $R_7$ is hydrogen, alkyl, aryl, substituted alkyl, or substituted aryl; and Y is a linking group selected from the group consisting of: alkylene, substituted alkylene, alkylidene, substituted alkylidene, arylene, or substituted arylene; and wherein Y additionally comprises a substituent that binds to the resin.

2. The apparatus of claim 1, wherein the resin is a macroporous resin.

3. The apparatus of claim 2 wherein the resin is selected from the group consisting of: PS-DVB, Chelex, polyamine, amine-modified styrene-divinylbenzene, aminated phenol-formaldehyde resin, or amine-modified acrylic resin.

4. The apparatus of claim 3 wherein the resin is PS-DVB.

5. The apparatus of claim 2 wherein the compound chelates a metal cation selected from the group consisting of: $Cu^{2+}$, $Ni^{2+}$, $Hg^{2+}$, $Cd^{2+}$, $Zn^{2+}$, and $Co^{2+}$.

6. The apparatus of claim 1, wherein the resin is microporous resin.

7. An apparatus comprising a resin attached to a compound comprising

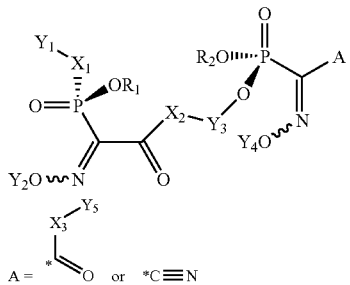

wherein: a starred atom denotes a point of attachment; $X_1$, $X_2$, and $X_3$ are independently selected from the group consisting of: O, $NR_3$, and S; $R_1$, $R_2$, $R_3$, $Y_1$, $Y_2$, $Y_3$, $Y_4$, and $Y_5$, are independently selected from the group consisting of hydrogen, alkyl, aryl, substituted alkyl, and substituted aryl; one of $Y_1$, $Y_2$, and $Y_3$ is selected from the group consisting of: alkylene, oxy-alkylene, aminoalkylene, thio-alkylene, —(CH2)$_n$C(=O)NH— wherein n is from 1 to 10, —(CH$_2$)$_n$C(=O)O— wherein n is from 1 to 10, arylene, substituted arylene, heteroarylene, and substituted heteroarylene; at least one of $R_1$ and $Y_1$ is not hydrogen; and at least one of $R_1$, $R_2$, $Y_1$, $Y_2$, $Y_4$, and $Y_5$ is hydrogen; and at least one of $R_1$ and $Y_1$ is not hydrogen; and
wherein the resin is attached to the compound through one of $Y_1$, $Y_2$, $Y_4$, or $Y_5$.

8. The apparatus of claim 7 wherein the resin is a macroporous resin.

9. The apparatus of claim 8, wherein the resin is selected from the group consisting of: PS-DVB, Chelex, polyamine, amine-modified styrene-divinylbenzene, aminated phenol-formaldehyde resin, or amine-modified acrylic resin.

10. The apparatus of claim 9 wherein the resin is PS-DVB.

11. The apparatus of claim 8 wherein the compound chelates a metal cation selected from the group consisting of: $Cu^{2+}$, $Ni^{2+}$, $Hg^{2+}$, $Cd^{2+}$, $Zn^{2+}$, and $Co^{2+}$.

12. The apparatus of claim 7 wherein the resin is a microporous resin.

13. An ion exchange apparatus comprising: a macroporous resin; and, attached to the resin a ligand having a structural formula:

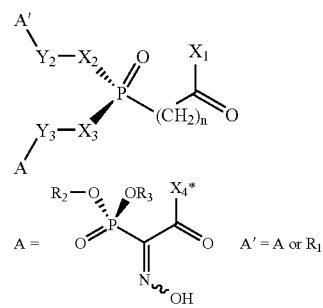

wherein: a starred atom denotes a point of attachment; N~O denotes a bond that represents the Z or E isomeric form; $X_1$, $X_2$, $X_3$ and $X_4$ are independently selected from the group consisting of: O, $NR_4$, and S; $X_1$ is attached directly to the resin; $Y_2$ and $Y_3$ are independently selected from the group consisting of: alkylene, oxyalkylene, aminoalkylene, thio-alkylene, arylene, substituted arylene, hetereoarylene, and substituted heteroarylene; $R_1$, $R_2$, $R_3$, and $R_4$ are independently selected from the group consisting of: hydrogen, alkyl, aryl, substituted alkyl, and substituted aryl; and n is from 1 to 5.

14. The apparatus of claim 13 wherein n=1 to provide a methylene group, and the methylene group is derivatized to form a hydroxy-imino group.

* * * * *